(12) United States Patent
Burgess et al.

(10) Patent No.: US 6,340,750 B1
(45) Date of Patent: Jan. 22, 2002

(54) THROUGH BOND ENERGY TRANSFER IN FLUORESCENT DYES FOR LABELLING BIOLOGICAL MOLECULES

(75) Inventors: Kevin Burgess, Bryan; Richard Gibbs, Houston, both of TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 09/460,718

(22) Filed: Dec. 14, 1999

Related U.S. Application Data

(60) Provisional application No. 60/112,711, filed on Dec. 18, 1998.

(51) Int. Cl.[7] .................. C07H 19/04; C07H 21/00; C09K 11/06; G01N 21/01; G01N 21/64

(52) U.S. Cl. .............. 536/26.6; 536/25.32; 252/301.16; 422/82.06; 422/82.07

(58) Field of Search .......................... 435/6, 91.1, 183, 435/283.1, 287.2; 436/94; 536/23.1, 24.3, 24.33, 25.32, 25.3, 26.6, 26.41; 252/301.16; 422/82.06, 82.07

(56) References Cited

PUBLICATIONS

Tyagi et al., Molecular Beacons: Probes that fluoresce upon hybridization. Nature Biotechnology 14, 303–308, Mar. 1996.*

Benson et al., Heterodimeric DNA–binding dye designed for energy transfer: synthesis and spectroscopic properties. Nucleic Acids Res. 21, 5727–5735, Dec. 1993.*

Kollmannsberger et al., Electrogenerated chemiluminescence and proton–dependent switching of fluorescence: functionalized difluoroboradiaza–s–indacenes. Angew. Chem. Int. Ed. Engl. 36, 1333–1335, 1997.*

Geohegan, Improved method for converting an unmodified peptide to an energy –transfer substrate for a proteinase. Bioconjugate Chem. 7, 385–391, May–Jun. 1996.*

A Rapid Method for Determining Sequences in DNA by Primed Synthesis with DNA Polymerase, F. Sanger, and A. R. Coulson, *J. Mol Biol.*, 1975, 94, 441–8.

DNA sequencing with chain termination inhibitors, F. Sanger, S. Nicklen, and A. R. Coulson, *Proc. Natl. Acad. Sci. U.S.A.*, 1977, 74, 5463–5467.

Fluorescence detection in automated DNA sequence analysis, L. M. Smith, J. Z. Sanders, R. J. Kaiser, P. Hughes, C. Dodd, C. R. Connell, C. Heiner, S. B. Kent, and L. E. Hood, *Nature*, 1986, 321, 674–9.

Large–Scale and Automated DNA Sequence Determination, T. Hunkapiller, R. J. Kaiser, B. F. Koop, and L. Hood, *Science*, 1991, 254, 59.

Large–Scale DNA Sequencing, T. Hunkapiller, R. J. Kaiser, B. F. Koop, and L. Hood, *Anal. Biotech.*, 1991, 2, 92–101.

The Future of DNA Sequencing, L. M. Smith, *Science*, 1993, 262, 530–2.

A system for rapid DNA sequencing with fluorescent chain–terminating dideoxynucleotides, J. M. Prober, G. L. Trainor, R. J. Dam, F. W. Hobbs, C. W. Robertson, R. J. Zagursky, A. J. Cocuzza, M. A. Jensen, and K. Baumeister, *Science*, 1987, 238, 336.

Energy Transfer Primers: A New Fluorescence Labeling Paradigm for DNA Sequencing and Analysis, J. Ju, A. N. Glazer, and R. A. Mathies, *Nature Med.*, 1996, 2, 246–9.

(List continued on next page.)

*Primary Examiner*—Ethan Whisenant
*Assistant Examiner*—Frank Lu
(74) *Attorney, Agent, or Firm*—Baker Botts, L.L.P.

(57) ABSTRACT

Fluorescent energy transfer cassettes that allow through bond energy transfer and have a succinimidyl ester functionality suitable for affecting them to biomolecules or provided and are applied to high throughput DNA sequencing.

8 Claims, 13 Drawing Sheets a Through space FET from a donor dye D to an acceptor dye A; b through bond FET.

a through space *FET* b through bond *FET*

OTHER PUBLICATIONS

Fluorescence energy transfer dye–labeled primers for DNA sequencing and analysis, J. Ju, C. Ruan, C. W. Fuller, A. N. Glazer, and R. A. Mathies, *Proc. Natl. Acad. Sci. USA,* 1995, 92, 4347–51.

Ultra–High–Speed DNA Sequencing Using Capillary Electrophoresis Chips, A. T. Woolley, and R. A. Mathies, *Anal. Chem.,* 1995, 67, 3676–80.

Rapid Sizing of Short Tandem Repeat Alleles Using Capillary Array Electrophoresis and Energy–Transfer Fluorescent Primers, Y. Wang, J. Ju, B. A. Carpenter, J. M. Atherton, G. F. Sensabaugh, and R. A. Mathies, *Anal. Chem.,* 1995, 67, 1197–203.

Design and Synthesis of Fluorescence Energy Transfer Dye–Labeled Primers and Their Application for DNA Sequencing and Analysis, J. Ju, I. Kheterpal, J. R. Scherer, C. Ruan, C. W. Fuller, A. N. Glazer, and R. A. Mathies, *Analytical Biochem.,* 1995, 231, 131–40.

Energy Transfer Primers with 5– or 6–Carboxyrhodamine–6G as Acceptor Chromophores, S.–C. Hung, J. Ju, R. A. Mathies, and A. N. Glazer, *Analytical Biochem.,* 1996, 238, 165–70.

Continuous, On–line DNA Sequencing Using Oligodeoxynucleotide Primers With Multiple Fluorophores, J. A. Brumbaugh, L. R. Middendorf, D. L. Grone, and J. L. Ruth, *Proc. Natl. Acad. Sci.,* 1988, 85, 5610–4.

A Single Residue in DNA Polymerases of the *Escherichia coli* DNA Polymerase I Family is Critical for Distinguishing between Deoxy– and Dideoxyribonucleotides, S. Tabor, and C.C. Richardson, *Proc. Natl. Acad. Sci. USA,* 1995, 92, 6339–6343.

Cassette Labeling for Facile Construction of Energy Transfer Fluorescent Primers, J. Ju, A. N. Glazer, and R. A. Mathies, *Nucleic Acids Res.,* 1996, 24, 1144–8.

Electrophoretically Uniform Fluorescent Dyes for Automated DNA Sequencing, M. L. Metzker, J. Lu, and R. A. Gibbs, *Science,* 1996, 271, 1420–2.

Comparison of Fluorescence Energy Transfer primers with Different Donor–Acceptor Dye Combinations, S. Hung, R.A. Mathies, and A. N. Glazer, *Analytical Biochemistry,* 1998, 255, 32–8.

A Convenient Synthesis of Acetylenes: Catalytic Substitutions of Acetylenic Hydrogen with Bromoalkenes, Iodoarenes, and Bromopyridines, K. Sonogashira, Y. Tohda, and N. Hagihara, *Tetrahedron Lett.,* 1975, 4467–70.

Stepwise Synthesis of Substituted Oligo(phenylenevinylene) via an Orthogonal Approach, T. Maddux, W. Li, and L. Yu, *J. Am. Chem. Soc.,* 1997, 119, 844–5.

Synthesis of Sequence Specific Phenylacetylene Oligomers on an Insoluble Solid Support, J. K. Young, J. C. Nelson, and J. S. Moore, *J. Am. Chem. Soc.,* 1994, 116, 10841–2.

Iterative Divergent/Convergent Approach to Linear Conjugated Oligomers by Successive Doubling of the Molecular Length: A Rapid Route to a 128Å–Long Potential Molecular Wire, J. S. Schumm, D. L. Pearson, and J. M. Tour, *Angew. Chem., Int. Ed. Engl.,* 1994, 33, 1360–3.

Soluble poly(1,4–phenyleneethynylene)s, R. Giesa, and R. C. Schulz, *Makromol Chem.,* 1990, 191, 857–67.

Luminescent Alkoxy–Functionalized Polyphenylenes, J. L. Reddinger, and J. R. Reynolds, *Abstr. Papers Am Chem. Soc.,* 1996, 211, 530–1.

Fluorescence Studies of Poly(p–phenyleneethynylene)s: The Effect of Andiracene Substitution, T. M. Swager, C. J. Gil, and M. S. Wrighton, *J. Phys. Chem.,* 1995, 99, 4886–93.

Efficient Solid–State Photoluminescence in New Poly(2, 5–dialkoxy–p–phenyleneethynylene)s, C. Weder, and M. S. Wrighton, *Marcomolecules,* 1996, 29, 5157–65.

Energy Transfer in Dendritic Macromolecules: Molecular Size Effects and the Role of an Energy Gradient, C. Devadoss, P. Bharathi, and J. S. Moore, *J. Am. Chem. Soc.,* 1996, 118, 9635–44.

Phenylacetylene Dendrimers by the Divergent Convergent, and Double–Stage Convergent Methods, Z. Xu, M. Kahr, K. L. Walker, C. L. Wilkins, and J. S. Moore, *J. Am. Chem. Soc.,* 1994, 116, 4537–50.

Conjugated Macromolecules of Precise Length and Constitution. Organic Synthesis for the Construction of Nanoarchitectures, J. M. Tour, *Chem. Rev.,* 1996, 96, 537–53.

A Molecular Photonic Wire, R. W. Wagner, and J. S. Lindsey, *J. Am. Chem Soc.,* 1994, 116, 9759–60.

Boron–dipyrromethene Dyes for Incorporation in Synthetic Multi–pigment Light–harvesting Arrays, R. W. Wagner, and J. S. Lindsey, *Pure & Appl. Chem.,* 1996, 68, 1373–80.

Heterodimeric DNA–binding dyes designed for energy transfer: synthesis and spectroscopic properties, S.C. Benson, P. Singh, A.N. Glazer, *Nucleic Acids Res.* 1993, 2I, 5727–35.

New energy transfer dyes for DNA sequencing, L.G. Lee, S.L. Spurgeon, C.R. Heiner, S.C. Benson, B.B. Rosenblum, S.L. Menchen, R.J. Graham, A. Constantinescu, K.G. Upadhya, J.M. Cassel, *Nucleic Acids Research* 1997, 25, 2816–22.

Difluorboryl–Komplexe von Di– und Tripyrrylmethenen, A. Treibs, F.H. Kreuzer, *Liebigs Ann. Chem.* 1968, 718, 208–23. BODIPY = 4,4–difluoro–4–bora–3a,4a–diaza–s–indacene.

Synthesis of 2, 6–Diethyl–3–methacroyloxymethyl–1, 5, 7, 8–tetramethylpyrromethene–$BF_2$ for the Preparation of New Solid–State Laser Dyes, T. Chen, J.H. Boyer, M.L. Trudell, *Heteroatom. Chem.* 1997, 8, 51–4.

Directed Electrophilic Cyclizations: Effecient Methodology for the Synthesis of Fused Polycyclic Aromatics, M.B. Goldfinger, K.B. Crawford, T.M. Swager, *J. Am. Chem. Soc.* 1997, 119, 4578–4593.

Anthryloliogothienylporphyrins: Energy Transfer and Light– Harvesting Systems, M.S. Vollmer, F. Wurthuer, F. Effenberger, P. Emele, D.U. Meyer, e. al, *Chem. Eur.. J.* 1998, 4, 260–9.

Steroid–Bridged Anthryloligothienylporphyrins: Synthesis and Study on the Intramolecular Energy Transfer, M.S. Vollmer, F. Effenberger, T. Stumpfig, A. Hartschuh, H. Port, H.C. Wolf, *J. Org. Chem.* 1998, 63, 5080–7.

\* cited by examiner

Figure 1. a Through space FET from a donor dye D to an acceptor dye A; b through bond FET.

a through space *FET* b through bond *FET* aa  $R^1 = R^2 = a$
ab  $R^1 = a, R^2 = b$ aa  $R^1 = R^2 = a$
ab  $R^1 = a, R^2 = b$ a R = H
b R = Et

Scheme 1. Syntheses of the cassettes 1 and 2, a) CH2Cl2 reflux: b) BF3•OEt2, NEt3, MePh, 80 °C, 26% (2 steps) for 3a and 39% (2 steps) for 3b; c) HCCTMS, NEt3, cat. Pd(PPh3)4, cat. CuI, MePh 60 °C, 99% for a and 96% for b; d) TBAF, THF, 0 °C, 60% for a and 58% for b; e)( 4a, NEt3, cat. Pd(PPh3)4, cat. CuI, MePh 50 °C, 96%; f)4a or 4b, NEt3, cat. Pd(PPh3)4, cat. CuI, MePh 80 °C, 65% for 1aa and 23% for 1ab; g) 4a, NEt3, cat. Pd(PPh3)4, cat. CuI, MePh 45 °C, 83%; f) 4a or 4b, NEt3, cat. Pd(PPh3)4, cat. CuI, MePh 80°, 65% for 1aa and 17% for 1ab.

Table 1. Important spectroscopic data for compounds 4, and the cassettes 1 and 2.

| | λmax (abs)[a] (nm) | λmax (ems)[b] (nm) | energy transfer (ET) efficiency [b,c] (%) |
|---|---|---|---|
| 4a | 504 | 515 | - |
| 4b | 529 | 543 | - |
| 1aa | 504 | 515 | - |
| 1ab | 505 and 529 | 542 | >90 |
| 2aa | 504 | 516 | - |
| 2ab | 505 and 529 | 543 | >90 |

| | ratios of fluorescence intensities[c] | |
|---|---|---|
| 4a | - | |
| 4b | - | |
| 1aa | 1aa:4a | 1.5: 1.0 |
| 1ab | 1ab:4b | 2.2: 1.0 |
| 2aa | 2aa:4a | 1.6: 1.0 |
| 2ab | 2ab:4b | 1.7: 1.0 |

[a] in CHCl$_3$. [b] where ET = {1 − (fluorescence intensity of donor emission in cassette)/(fluorescence intensity of donor alone)} × 100% [c] excitation at 488 nm.

FIG. 4 donor 1a-e acceptors:

| | R1 | R2 | R3 |
|---|---|---|---|
| a | Me | H | Me |
| b | Me | Et | Me |
| c | H | H | 2-MeOC6H4 | acceptors:

|   | R⁴  |
|---|-----|
| d | H   |
| e | OMe |

4a

THROUGH BOND ENERGY TRANSFER IN FLUORESCENT DYES FOR LABELLING BIOLOGICAL MOLECULES

CROSS REFERENCE TO RELATED APPLICATIONS

This application claims the benefit of U.S. Provisional Patent Application entitled "Through Bond Energy Transfer in Fluorescent Dyes for Labelling Biological Molecules," Ser. No. 60/112,711 filed Dec. 18, 1998.

RIGHTS IN THE INVENTION

This invention was made in part with United States Government support under grant number HG01745 awarded by the National Institute of Health, and the United States Government has certain rights in the invention.

TECHNICAL FIELD OF THE INVENTION

The present invention relates in general to the field of DNA sequencing and, more particularly, to through bond energy transfer in fluorescent dyes for labelling biological molecules.

BACKGROUND OF THE INVENTION

Methods routinely applied for high throughput DNA sequencing have oscillated between two embodiments of the Sanger scheme. [A1, A2] Fluorescence detection dominates throughout, [A3] but the factor that distinguishes the approaches is that the labels can be situated in the primer (dye-primers) or in the terminating fragments (dye-terminators). Both methods have been, and continue to be, used. [A4–A6]

Early dye-primer technology featured one fluorescent flag per primer. Four reactions were performed with each of the ddNTP's using the "workhorse tags", i.e., JOE, TAMRA, ROX, and FAM. These four reactions were mixed after production of a nested set of chain terminated DNA fragments, and analyses were performed via gel electrophoresis in one lane with a static detector.

Dye terminator strategies [A7] have the advantage that only one reaction is required to produce a nested set of chain terminated DNA fragments labeled with fluorescent groups appropriate to the four ddNTP's. The (unlabeled) primers used are also cheaper to produce than the corresponding fluorescently labeled ones. Moreover, in contrast to dye-primer strategies, pausing bands are invisible to fluorescence detection when the label is present only in the terminator. The disadvantage of dye-terminators is that not all of the relatively precious labeled component is incorporated into the complement whereas all the fluorescence is retained in the complement if the dye primer method is used.

A significant advance in dye-primer methodology occurred when it was realized that the fluorescence signal could be enhanced by approximately ten-fold when two labels were used in the following way. [A9] One was selected to absorb relatively high energy photons; energy transfer though space to the second fluorescent group would then lead to emission at a lower wavelength. Specifically, FAM was (and is) used to harvest the irradiation, then convey energy through space to either JOE, TAMRA, or ROX. The ten-fold enhancement obtained is significant because it facilitates use of less reagents (dye-primer, enzyme, dNTPs, ddNTPs, etc.), and/or lessens the need to concentrate the reactions before gel electrophoresis and detection.[A9–A13] Energy transfer enhancement of fluorescence is more efficient than other systems wherein two identical fluorescent labels per primer have been used to enhance sensitivity.[A14]

The utility of the dye-terminator approach has also been enhanced, but in this case the development was one in molecular biology. Tabor and Richardson showed that some mutated DNA polymerases favor incorporation of labeled ddNTPs. [A15] These enzymes are more expensive than the wild type, but they can be obtained in significant quantities via over-expression. Use of these DNA replicating enzymes leads to more efficient use of ddNTPs in Sanger sequencing, and this is particularly important when the ddNTP bears a label.

The state of the art in high throughput sequencing is such that both dye-primers and dye terminators are used. Typically, cloned genomic fragments are randomly sheared and subcloned into specialized sequencing vectors, i.e., the "shot-gun" approach. Doubly labeled dye-primers that complement the specialized vector arms are then used to begin the sequencing operation; a compelling advantage of this is that only a limited repertoire of these expensive primers is required. Primer walking is then used to extend the sequence information obtained. However, the primer walking steps, and sequencing of regions riot-covered by the shot-gun/primer walking process, require primers that are tailor made to those particular sequences (rather than to a restriction site sequences). Syntheses of many different doubly labeled dye-based primers cannot be justified, so a different approach is used. In fact, it is cost effective to use labeled ddNTPs/mutant DNA replicating enzymes at this stage, therefore obviating the need for extensive dye-primer syntheses.

SUMMARY OF THE INVENTION

Fluorescent energy transfer cassettes are reported. Unique features of these are that they allow through bond energy transfer and have a succinimidyl ester functionality suitable for attaching them to biomolecules. The relevance of this design concept to high throughout DNA sequencing is discussed.

This disclosure outlines a general design principle for new fluorescent dyes to be applied in high throughput DNA sequencing protocols (e.g., The Genome Project) and other applications in biotechnology.

Fluorescent dyes for DNA sequencing and other biotechnological applications can be produced in the following way. A UV-absorbing chromophore is selected that will absorb relatively strongly at the wavelength emitted by the source chosen for the application under consideration. Organic synthesis is then performed to incorporate this chromophore into a molecule wherein the chromophore is conjugated with a molecular entity having desirable fluorescence emission properties. In DNA sequencing, the latter group would be one with a strong, narrow bandwidth, emission at a distinctly different wavelength to the other dyes used in the sequencing method. The UV chromophore must absorb at a lower wavelength than the fluorescence emitter, and it is highly desirable that the chromophore and fluorescence emitter be placed at opposite ends of the conjugated system (not in the middle). In the anticipated mode of action of these dyes, the UV absorbing group would harvest radiation from the excitation source and transmit it through the conjugated system to the fluorescence emitter which would then fluoresce.

The new fluorescent dyes should also preferably have the following properties:

(i) manageable solubility characteristics;
(ii) functionality that allows them to be conveniently attached to nucleotides (or other biomolecules);
(iii) similar structures when used as sets for DNA sequencing, thus giving near tagged DNA fragments with similar gel mobilities;
(iv) chemical stability;
(v) chemical accessibility (i.e., can be obtained via convenient syntheses); and,
(vi) functional groups which facilitate convenient and economical incorporation of the labels.

According to one embodiment, the design principle disclosed here provides dyes that can be designed to:

harvest radiation (from lasers and similar devices) in regions of the electromagnetic spectrum that cannot be efficiently absorbed by the dyes currently used for DNA sequencing, thus allowing a wider variety of light source wavelengths to be used;

fluoresce in a greater wavelength range than the four dye detection system most often used at present (i.e., JOE, TAMRA, ROX, FAM) allowing greater resolution of the fluorescence emission from the dyes giving a more accurate read in DNA sequencing experiments;

give more intense fluorescent emission on irradiation with a usable source than is currently possible using JOE, TAMRA, ROX, and FAM, thus giving increased sensitivity and enabling smaller amounts of samples to be detected;

give fluorescence emission from a usable source that is comparable or superior to the through space energy transfer dyes introduced by Mathies, and by Gibbs, and their coworkers;

be introduced more conveniently and economically than the through space energy transfer dyes introduced by Mathies, and by Gibbs, and their co-workers; and, be useful in both the "dye-primer" and the "dye-terminator" approaches to DNA sequencing.

Sets of fluorescent dyes would be prepared such that one UV absorbing group was paired with four different fluorescent emitter moieties, each with clearly different emission wavelengths. This would allow strong fluorescence at four clearly distinguishable wavelengths.

There is also potential for two different sets of sequencing reactions to be mixed and analyzed in a single gel electrophoresis run. Thus, if two UV absorbing molecules that absorbed in mutually exclusive regions of the spectrum were each paired with four dyes, emission would only occur in one set if the absorbance were tuned to one UV absorbing group. Alternatively, eight different dyes could be coupled with one or two UV absorbing groups (four each) to achieve the same end.

BRIEF DESCRIPTION OF THE DRAWINGS

A more complete understanding of the invention and its advantages will be apparent from the detailed description taken in conjunction with the accompanying drawings in which:

FIG. 4 is a table illustrating important spectroscopic data for compounds 4, and the cassettes 1 and 2.

FIG. 5A shows the anthracene derivative donors, while FIGS. 5B and 5C show the BODIPY acceptor units.

FIG. 9A shows the conversion of 9,10-dibromoanthracene to compound 3.

FIG. 9B shows the linking of compound 3 to compounds 2a–e to afford dyes 1 a–e.

FIG. 9C shows the chemical structures of compounds 2a–c, and

FIG. 9D shows the chemical structures of compounds 2d–e.

DETAILED DESCRIPTION OF THE INVENTION

Figure 1A:
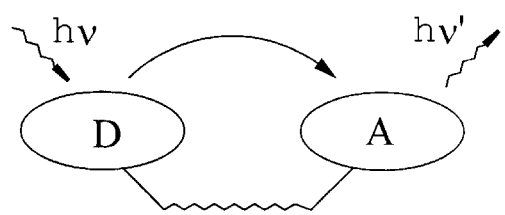
FIGS. 1a and 1b are schematic diagrams illustrating energy transfer "through space" and energy transfer "through bonds," respectively, for the production of fluorescent labels for biological systems.

The preferred embodiments of the present invention and its advantages are best understood by referring to the FIGS. 1 through 4 of the drawings according to the teachings of the invention.

Several conclusions may be made based on the discussions above. First, enhancement of fluorescence emission is desirable. Second, both dye-primer and dye-terminator approaches are viable, and the selection of one over the other is not a clear cut choice. It is possible, for instance, that if the dye-terminator methodology were improved then most sequencing reactions might be done that way. If they were, the number of reactions necessary to generate DNA complements would be reduced by a factor of four relative to dye-primer approaches (since the four different ddNTP's can be mixed), and pausing bands would become invisible.

There are at least two ways to improve the utility of the dye-terminator approach. Energy transfer emission enhanced fluorescent tags for ddNTP's have not yet been developed, so work in this area is very likely to be useful. Another avenue to explore is to devise completely new fluorescent labels for ddNTP's.

Superior dye-primer labels must overcome the false priming and mobility shift problems, and the experimental inconveniences associated with label incorporation. When singly labeled dye primers are used, mobility differences are compensated by virtual corrections to the data after detection but prior to output of the read. Almost all of the work with double dye primers involves labels supported on T-analogs which constitute part of the primer sequence. Those systems can be vulnerable to false priming due to these unnatural nucleotides. Moreover, the mobility correction varies with sequence and cannot always be adequately accommodated by virtual corrections. To address this problem, Mathies and co-workers designed a system that they term "cassette labeling". [A16] In this method, the primer syntheses are performed in such a way that the first fluorescent base is added at the 5'-termini of the primers, then six more cycles of phosphoramidite couplings are performed using deoxyribose units with no purine or pyrimidine functionalities. Finally, the other label is added at the end of this chain. The primers formed in this way are less vulnerable to false priming, and the DNA complements derived from them have improved mobility characteristics and exhibit less fluorescence quenching. However, this strategy is not ideal for several reasons. Most important of these are the fact that these primers require seven more coupling steps than are required to generate the primer sequence. The word "cassette" is inappropriate for this system because it implies that the dye labels with the appropriate spacing are simply slotted in; in fact, they are built on the end of the primer in a multi-step operation which must be repeated for each primer. Second, the linker between the two labels is flexible. Consequently, the fluorescence emission will be the result of averaged conformational states which may vary according to the different environments of the label system. Third, the radiation that can be used to excite the labels must be chosen within relatively restrictive wavelength regions (e.g. 488 nrn or 154 nrn source, but not ones much lower in wavelength). An eight dye system with four responding to one excitation wavelength and four responding at another would be extremely hard or almost impossible to develop given the dyes available. Finally, the issue of gel mobilities is not a solved problem because different conformational states may still be present in ratios that vary with the peripheral primer sequence. Energy transfer systems based on BODIPY dyes have been introduced for enhanced sensitivity and improved gel mobility factors in DNA sequencing, [A17] but the concerns outlined above still apply. [A18]

Dye-primer methodologies may be improved by generating a double-dye cassette that could be conveniently incorporated into a primer in one step. This cassette is preferably relatively rigid to minimize sequence dependent mobility variations.

No compounds of the this type (i.e., fluorescent compounds having a UV-harvesting group in conjugation with a fluorescence emitter) have been reported by others specifically for DNA sequencing or, as far as we are aware, for other applications in biotechnology. However, compounds which harvest UV radiation, and transmit it to a fluorescent group via a conjugated system have been reported. This section summarizes highlights from that literature.

Polymers and oligormers of type I are prepared via Sonogashira couplings of aryl halide and arylalkyne components. This coupling reaction is more efficient than the Wadsworth-Emmons reaction generally used to produce the corresponding systems with alkene rather than aryne linkages. In fact, solid phase syntheses of these materials are possible as a direct consequence of the efficiency of the Sonogashira coupling.

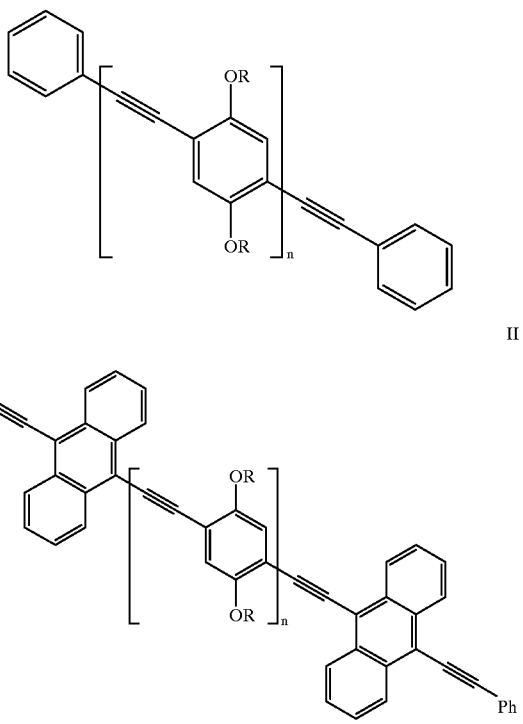

Extended aryl alkyne molecules are not particularly soluble in any common solvent, but the alkoxide subsituents shown in structure I can be used to give appreciable solubilities. In nearly all literature on these compounds the "OR" functionalities are O-hydrocarbons included for compatibility with organic media, although in at least one case a water soluble system has been produced when R was a sulfonated benzylic group.

Molecules of type I are chemically robust. They would not, for instance, react or decompose under the thermal cycling conditions used for enzymatic generation of DNA components.

The spacing between repeat units in the polymers I is approximately 6.75 Å. This rigidity could be exploited to hold a UV absorbing group and a fluorescence emitter at a relatively invariant and easily estimated separation.

Photophysical properties of framework I are such that absorption occurs at around 448 nm and fluorescence emission occurs at 474 nm (n=~22). High fluorescent quantum yields are often observed (ca 0.8 to 0.9 for many molecules of type I) presumably because the rigidity of the system precludes bond motions that would otherwise result in radiationless decay. Moreover, the emission spectrum tends to be relatively sharp, much sharper than the absorption spectrum. The most relevant property of these materials to this project is the energy transfer properties seen for molecules like polymer II. This material emits at 524 nm irrespective of the wavelength of the absorption. It appears that random excitation of the polymer backbond transmits the energy to the low energy anthracene end group resulting in emission.25. The mechanism of energy transfer is "photonic", rather than through space, hence the rigid arylalkyne rods have been referred to as "molecular wires". The florescence quantum yield is not always high, however. If the low energy group is situated in a relatively central position in the polymeric chain, for instance, then the florescence quantum yield is low. However, placement of a high energy absorbing group at one termini and a low energy emitting group at the other facilitates tunable absorption and photonic relay to the low energy emitting group with high florescence quantum yield. Thus, a particular wavelength of the absorption can be determined by choosing a suitable high energy end-group, and the wavelength of emission can be similarly adjusted using a different group at the other terminus. These types of observations regarding the photophysical properties of repeating arylalkyne units have been reported for many ohgomeric. cyclic, dendric, and polymeric systems. Particularly relevant are systems which incorporate the so-called BODIPY dyes, prepared for goals that were not stated to include DNA sequencing.

In conclusion, dye-primer methodologies could be improved by generating a double-dye cassette that could be conveniently incorporated into a primer in one step. This cassette should be relatively rigid to minimize sequence dependent mobility variations.

The state of art in fluorescence-based DNA sequencing methodologies is to use four sets of two dyes, one set for each sequencing reaction, arranged such that through space fluorescence energy transfer (FET) enhances the emission of each set. [B1-B4] This leads to increased sensitivity hence more bases can be sequenced in each run. Typically, identical donor dyes are applied in each set so that irradiation at a single wavelength, usually 488 nm from argon lasers, can be used throughout. In a system wherein four dye sets are excited by one laser source, FET allows the dyes with longer fluorescence emission max values to absorb energy at 488 nm more efficiently. FET essentially increases the overlap of the absorption spectra of the acceptor dye with the exciting irradiation.

Figure 1B:
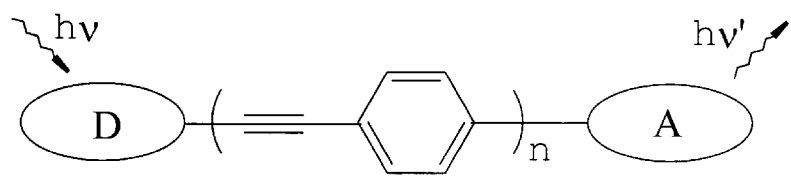
Figure 2A:
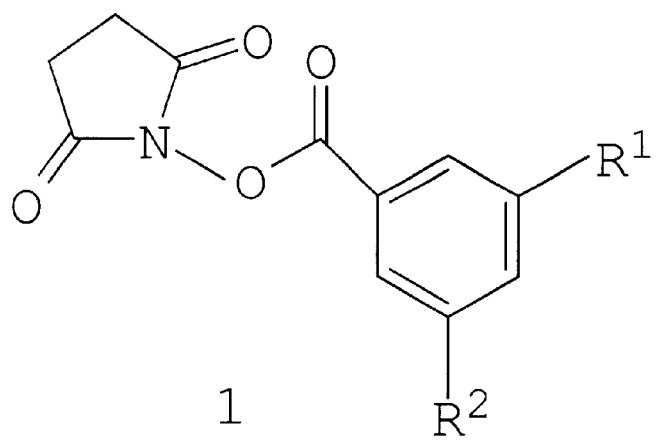
FIG. 2 is a diagram illustrating the structures of four cassettes used according to the teachings of the present invention for labeling DNA or other biological molecules.
Figure 2B:
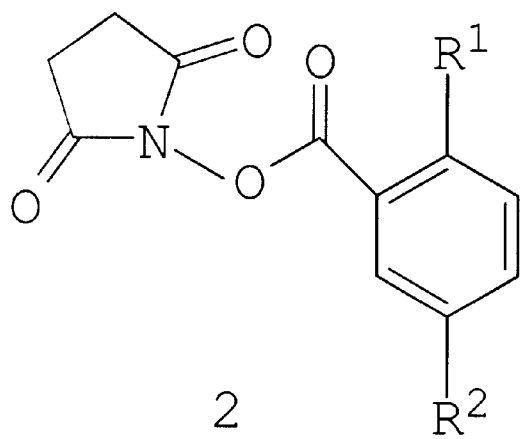
Figure 2C:
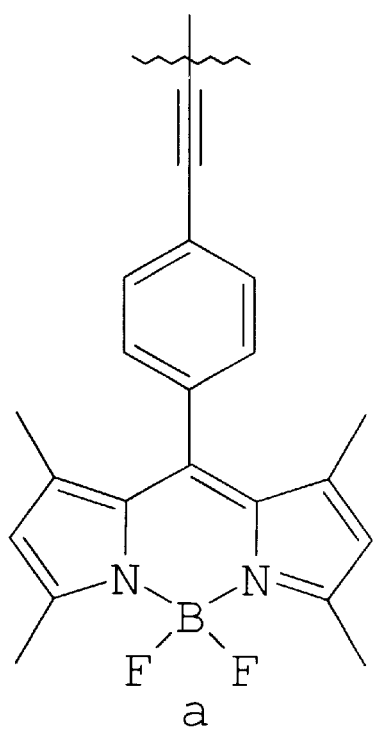
Figure 2D:
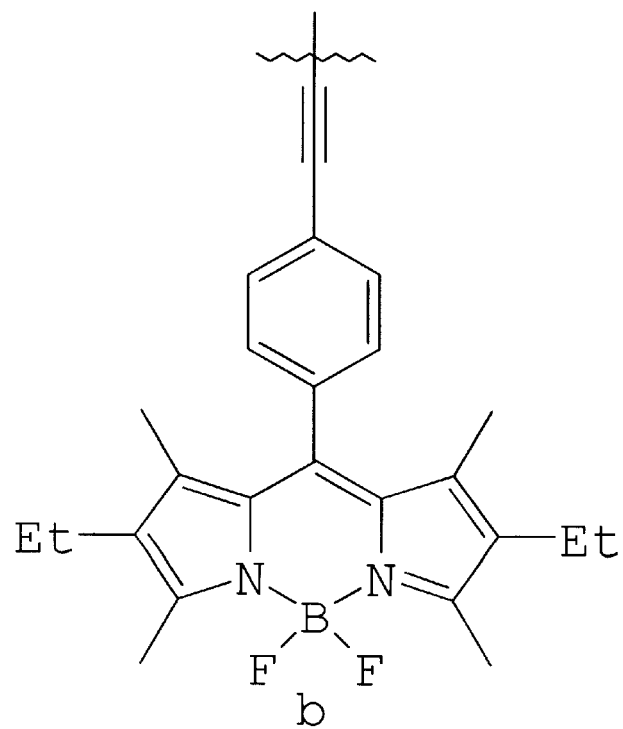
Figure 3A:
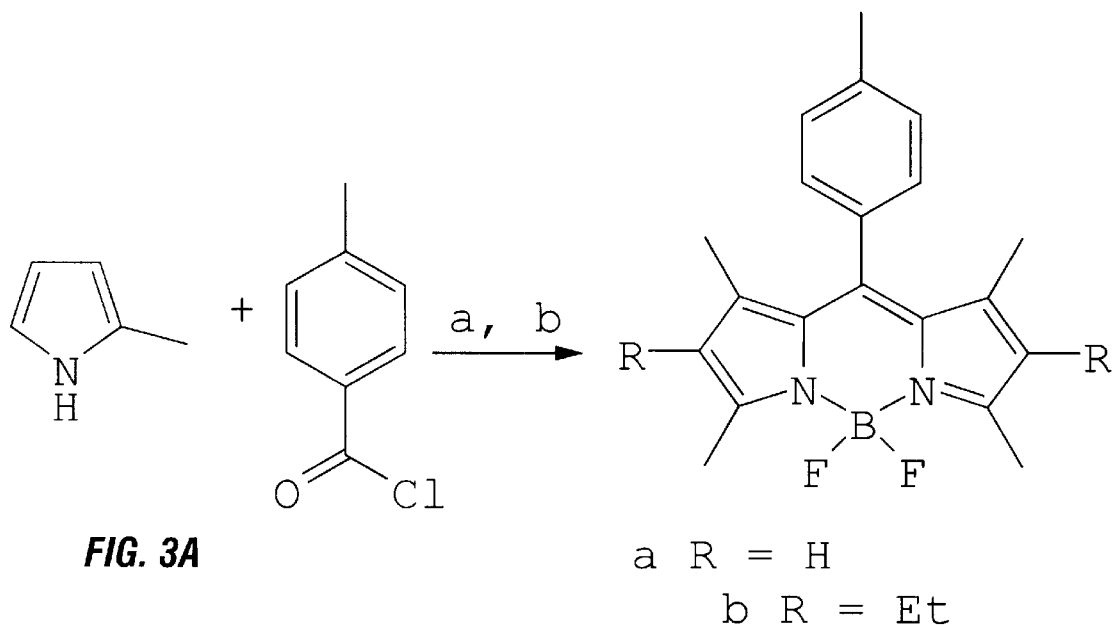
FIG. 3 is a diagram illustrating synthesis of cassettes 1 and 2. a) $CH_2CL_2$ reflux: b) $BF_3.OEt_2$, $NEt_3$, MePh, 80° C., 26% (2 steps) for 3a and 39% (2 steps) for 3b; c) HCCTMS, $NEt_3$, cat. $Pd(PPh_3)_4$, cat. CuI, MePh 60° C., 99% for a and 96% for b; d) TABF, THF, 0° C., 60% for a and 58% for b; e) 4a, $NEt_3$, cat $Ph(PPh_3)_4$, cat. CuI, MePh 50° C., 96%; f) 4a or 4b, $NEt_3$, cat. $Pd(PPh_3)_4$, cat. CuI, MePh 80° C., 65% for 1aa and 23% for 1ab; g) 4a, $NEt_3$, cat. $Pd(PPh_3)_4$, cat. CuI, MePh 45° C., 83%; f) 4a or 4b, $NEt_3$, cat. $Pd(PPh_3)_4$, cat. CuI, MePh 80° C., 65% for 1aa and 17% for 1ab.
Figure 3B:
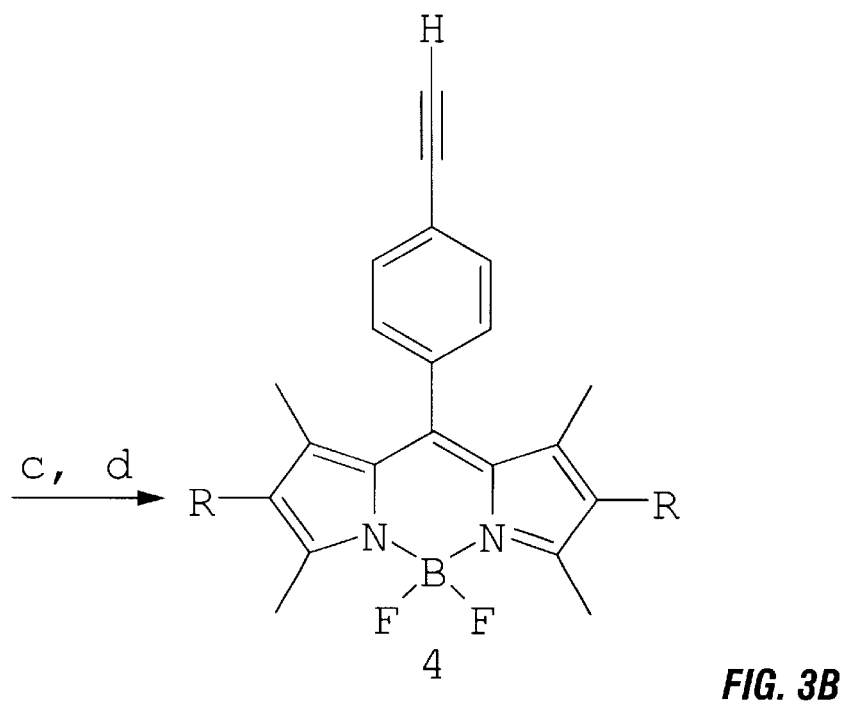
Figure 3C:
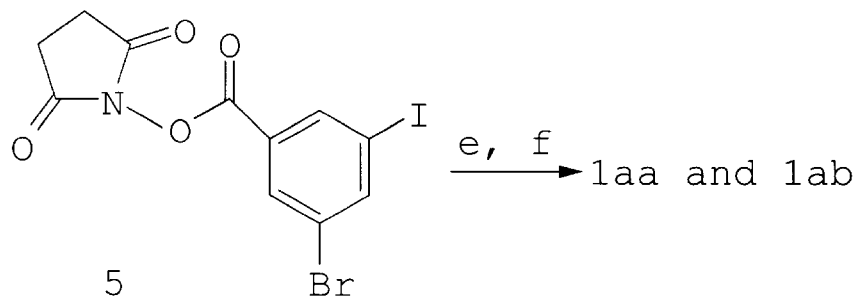
Figure 3D:
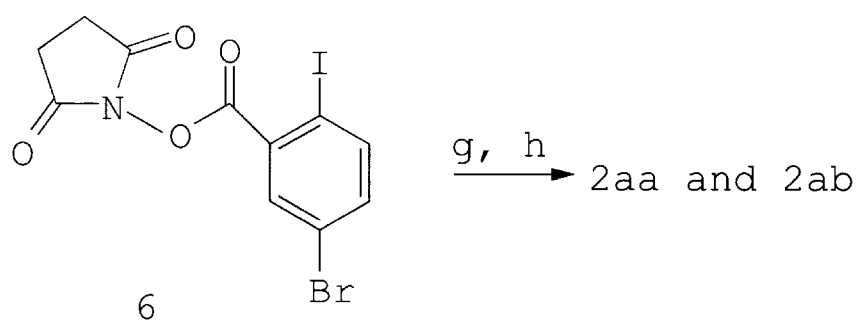
Figure 5A:
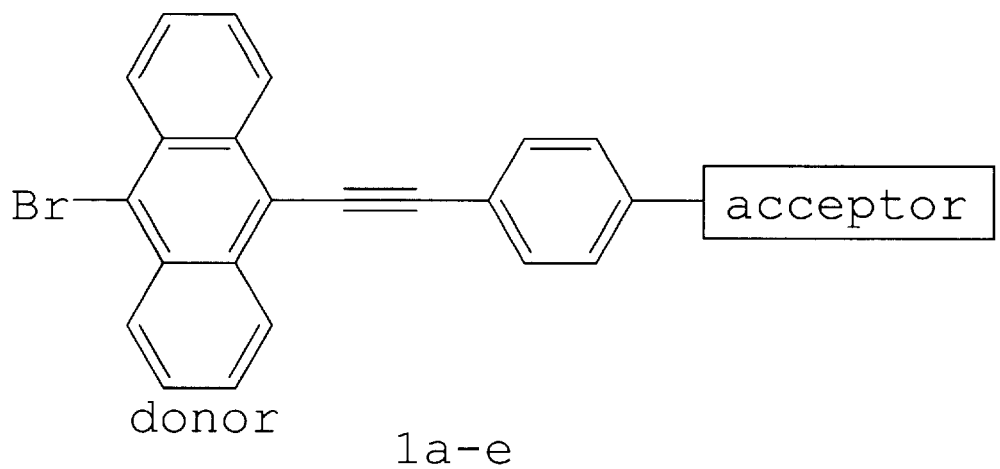
FIGS. 5A, 5B, and 5C depict donor and acceptor portions of the fluorescent dyes.
Figure 5B:
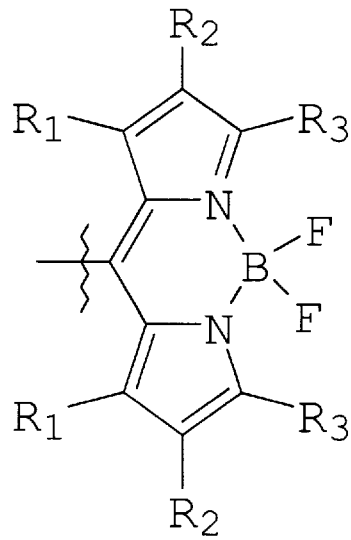
Figure 5C:
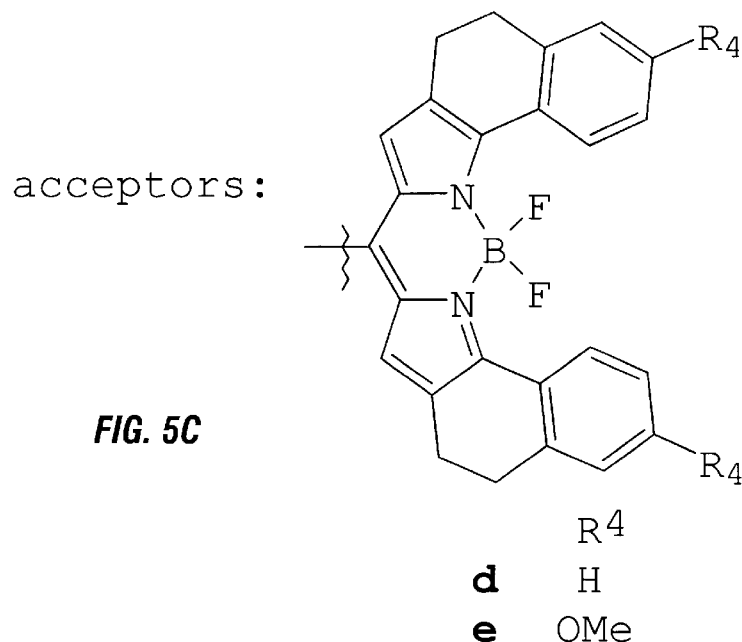
Figure 6:
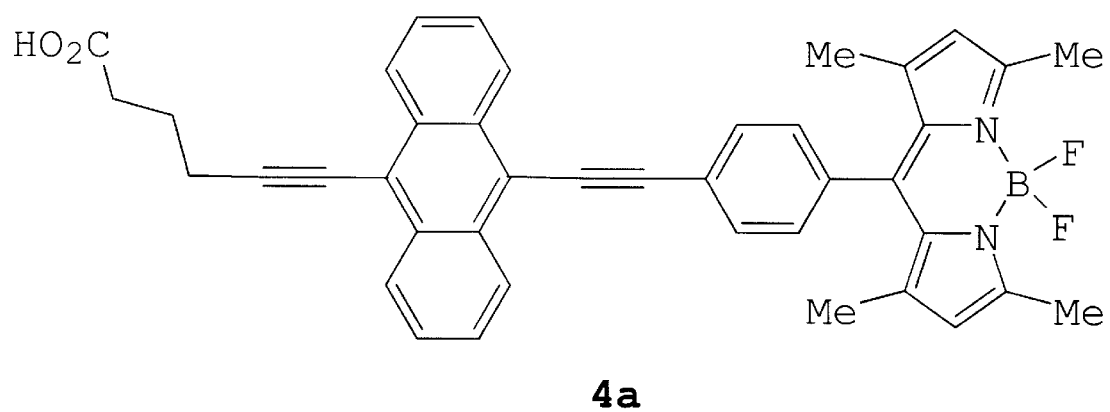
FIG. 6 depicts a dye suitable for coupling to DNA.

FIGS. 1a and 1b are schematic diagrams illustrating energy transfer "through space" and energy transfer "through bonds," respectively, for the production of fluorescent labels for biological systems. The first attempts to construct FET-based dye systems for DNA sequencing used donor and acceptor dyes attached to different nucleobases in a primer. This route to FET-based dye systems is experimentally inefficient if many dye-labeled primers must be produced, as in The Human Genome Project. Moreover, the only mechanism by which these dyes could transfer energy would be "through space." (FIG. 2).

Several groups have noted that FET between two dyes that are conjugated with each other can be remarkably efficient, and this property has been used to produce new materials with interesting photophysical properties. [B5-B9]However, to the best of our knowledge, such "through bond" energy transfer (FIG. 1b) has not yet been exploited in the production of fluorescent labels for biological systems.

Disclosed here are our preliminary efforts to form FET-dye cassettes for biological labeling that potentially allow energy to be transferred through bonds as well as through space. Specifically, the targets of this preliminary study are compounds 1aa, 1ab, 2aa, and 2ab. the issues to be addressed here are the syntheses of these compounds and, for 1ab, and 2ab, correlation of fluorescence properties related to orientation of the donor and acceptor fragments a and b, respectively.

FIG. 2 is a diagram illustrating the structures of four cassettes used according to the teachings of the present invention for labeling DNA or other biological molecules, and FIG. 3 is a diagram illustrating synthesis of cassettes 1 and 2.

Briefly, the cassettes 1aa, 1ab, 2aa, and 2ab were constructed as outlined in FIG. 2. The BODIPY [B10] framework of compounds 3 was prepared by condensing 4-iodobenzoyl chloride with the corresponding pyrrole, then reaction with $BF_3.OEt_2$ in a one-pot two-step process. [B11] Building blocks 4 were prepared from this produce via a Gonogashira coupling reaction [B12] with trimethylsilylethyne, then desilylation using tetra-n-butylammonium fluoride (TABF). BODIPY's 4a and b were then coupled to the core fragments 5 and 6 in the stepwise reactions indicted. These selective Sonogashira couplings exploited the difference in reactivity between aryl iodides and aryl bromides. [B13, B14]

FIG. 4 summarizes important spectroscopic data for the cassettes 1 and 2. The absorption spectra of the cassettes resemble the sum of the two individual chromophores, and the $_{max}$values are not shifted relative to their BODIPY constituents 4a/4b. Similarly, the fluorescence emission $_{max}$ values are not shifted relative to the corresponding acceptor fragment (4a or 4b) alone. The emission of the donor fragment 4a, however, is almost completely suppressed in the cassettes 1ab and 2ab implying that the energy transfer efficiency in these systems is very high. Possibly the most important data set in Table 1 is the ratio of fluorescence intensities when the cassettes are irradiated at 488 nm. The relative increase in fluorescence intensity is greatest for the meta-substituted systems 1ab showing that this arrangement of donor and acceptor fragments is preferred over the para-orientation in cassette 2ab.

Two embodiments of the invention are depicted below. These two dyes A and B have absorption and fluorescence emission spectra that are comparable with the concept designed herein. One has a functional group that allows the tag to be attached to an amino group of a modified DNA residue.

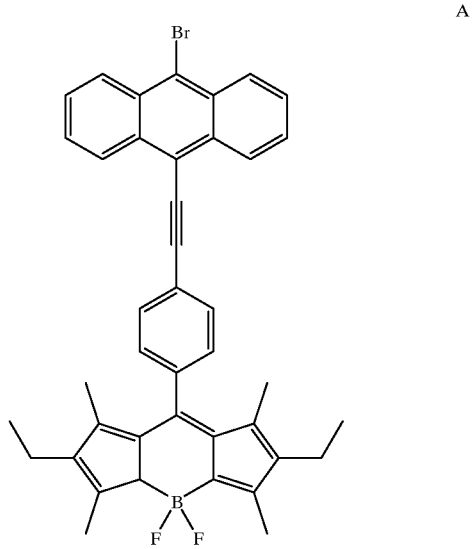

A

-continued

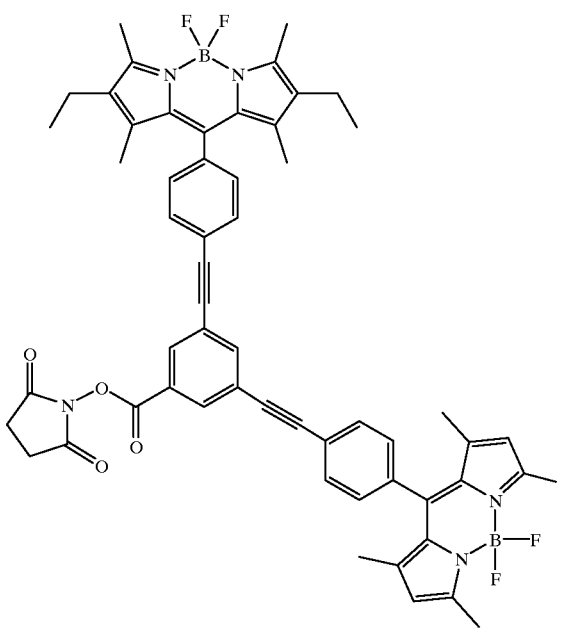

Dyes according to the invention may be used in sequencing reactions. For example, they may be attached to DNA oligomers in connection with the "dye-primer" sequencing method. Dideoxynucleoside triphosphate terminators may be tagged with the new dye systems in the "dye terminator" approach. Ideal combinations of dyes may be developed as desired, as well as optimizing water solubility and minimizing gel mobility shifts between the dye systems.

In the practice of the invention a multitude of UV absorbing and fluorescent emitting groups may be useful. Suitable UV absorbers may include, but are not restricted to, perylene, anthacene, tetracene, fluorescein, and some BODIPY dyes. Suitable emitters may include, but are not restricted to, fluorescein derivatives, rhodamine systems, BODIPYs, squareine and other relatively long wavelength emitters such as cyanine dyes. Energy transfer through space may be used in some members of the dye sets for convenience.

Additional embodiments of the invention are described in the paper attached as Appendix A.

Experiments are in progress to further understand the fluorescence properties of these molecules; determination of the relative contributions of through-space and through-bond energy transfer would be particularly interesting. Others have speculated that through space FET can dominate even in conjugated systems. [B15, B16] and a significant contribution via this mechanism could account for the higher fluorescence emission of the meta-cassette 1ab. In general, the type of cassettes introduced in this communication could have several attractive features. Specifically, through bond effects could add to the FET efficiency, the range of accessible $_{max}$ values may be greater due to through-bond energy transfer (an important factor in four-color DAN sequencing methodologies), and the donor and acceptor fragments are packaged in a single facilitating convenient introduction of the tag.

Experimental Section

Information related to experiments resulting in the above-described results is described below.

Characterization Data for the Cassettes. 1aa. mp 180 180° C. (dec.); $R_f$ 0.39 (45% EtOAc/hexanes); $^1$H NMR (CDCl$_3$, 300 MHz) δ1.41 (s, 12 H), 2.54 (s, 12 H), 2.91 (bs, 4 H), 5.98 (s, 4 H), 7.30 (d, J=8.4 Hz, 4 H), 7.67 (d, J=8.4 Hz, 4 H), 7.99 (t, J=1.5 Hz, 1 H), 8.26 (d, J=1.5 Hz, 2 H); $^{13}$C NMR (CDCl$_3$, 75 MHz) δ14.6, 25.6, 88.0, 91.0, 121.4, 123.1, 124.6, 126.2, 128.4, 131.1, 132.4, 132.9, 135.7, 139.8, 140.4, 142.9, 155.8, 160.6, 168.9; MS (FAB*) m/z 911 (M*); HRMS calcd for C$_{53}$H$_{43}$N$_5$O$_4$B$_2$F$_4$ [M*] 911.3454, found [M*] 911.3460. 1ab. mp 220° C. (dec.); $R_f$ 0.39 (35% EtOAc/hexanes); $^1$H NMR (CDCl$_3$, 300 MHz) δ0.97 (t, J=7.5 Hz, 6 H), 1.31 (s, 6 H), 1.42 (s, 6 H), 2.52 (s, 6 H), 2.54 (s, 6 H), 2.90 (q, J=7.3 Hz, 4 H), 2.92 (bs, 4 H), 5.99 (s, 2 H), 7.31 (d, J=8.1 Hz, 4 H), 7.66 (d, J=8.4 Hz, 2 H), 7.67 (d, J=8.4 Hz, 2 H), 7.99 (t, J=1.5 Hz, 1 H), 8.26 (m, 2 H), $^{13}$C NMR (CDCl$_3$, 75 MHz) δ11.9, 12.5, 14.6, 25.6, 87.9, 88.0, 91.0, 91.2, 121.4, 122.8, 123.1, 124.5, 124.6, 126.2, 128.4, 128.7, 130.4, 131.1, 132.3, 132.4, 133.0, 135.7, 136.6, 138.1, 138.9, 139.8, 140.4, 142.9, 154.1, 155.8, 160.7, 168.9; MS (FAB+) m/z 967 (M*); HRMS calcd for C$_{57}$H$_{51}$N$_5$O$_4$B$_2$F$_4$ [M+] 967.4081, found [M+] 967.4101. 2aa. mp 219–220° C.; $R_f$ 0.32 (40% EtOAc/hexanes); $^1$H NMR (CDCl$_3$, 300 MHz) δ1.42 (s, 12 H), 2.55 (s, 12 H), 2.95 (bs, 4 H), 5.99 (s, 4 H), 7.28–7.33 (m, 4 H), 7.66–7.79 (m, 6 H), 8.37 (d, J=1.7, 1 H); $^{13}$C NMR (CDCl$_3$, 75 MHz) δ14.57, 14.6, 25.8, 88.1, 88.8, 92.2, 97.3, 121.4, 123.3, 123.4, 123.6, 124.6, 128.3, 128.5, 129.8, 131.2, 132.4, 132.7, 134.3, 134.4, 135.9, 136.0, 142.9, 155.9, 160.3, 169.0; MS (FAB+) m/z 911 (M+); HRMS calcd for C$_{53}$H$_{43}$N$_5$O$_4$B$_2$F$_4$ [M+]611.3454, found [M*' 911.3460. 2ab. mp 215–216° C.; $R_f$ 0.32 (40% EtOAc/hexanes); $^1$H NMR (CDCl$_3$, 300 MHz) δ0.96 (t, J=7.5 Hz, 6 H), 1.31 (s, 6 H), 1.40 (s, 6 H), 2.28 (q, J=7.3 Hz, 4 H), 2.51 (s, 6 H), 2.54 (s, 6 H), 2.94 (bs, 4 H), 5.97 (s, 2 H), 7.27–7.32 (m, 4 H), 7.68–7.73 (m, 6 H), 8.38 (d, J=1.5 Hz, 1 H); $^{13}$C NMR (CDCl$_3$, 75 MHz) δ11.9, 12.5, 14.6, 14.7, 17.1, 25.7, 29.7, 88.1, 88.6, 92.3, 97.3, 121.4, 123.0, 123.4, 123.5, 124.6, 125.3, 126.8, 128.2, 128.3, 128.7, 129.0, 130.5, 131.1, 132.3, 132.7, 133.0, 134.35, 134.4, 135.8, 136.0, 136.6, 138.2, 139.0, 141.1, 143.0, 154.1, 155.8, 159.1, 160.2, 169.1; MS (FAB+) m/z 967 (M+); HRMS calcd for C$_{57}$H$_{51}$N$_5$O$_4$B$_2$F$_4$ [M+] 967,4081, found [M+] 967.4101.

Although the present invention and its advantage have been described in detail, it should be understood that various changes, substitutions, and alternatives can be made therein without departing from the spirit and scope of the present invention as defined by the appended claims.

The following references are incorporated herein by reference.

A1. A Rapid Method for Determining Sequences in DNA by Primed Synthesis with DNA Polymerase, F. Sanger, and A. R. Coulson, *J. Mol Biol.*, 1975, 94, 441–8.

A2 DNA sequencing with chain termination inhibitors, F. Sanger, S. Nicklen, and A. R. Coulson, *Proc. Natl. Acad. Sci. U.S.A.*, 1977, 74, 5463–5467.

A3 Fluorescence detection in automated DNA sequence analysis, L. M. Smith, J. Z. Sanders, R. J. Kaiser, P. Hughes, C. Dodd, C. R. Connell, C. Heiner, S. B. Kent, and L. E. Hood, *Nature*, 1986, 321, 674–9.

A4. Large-Scale and Automated DNA Sequence Determination, T. Hunkapiller, R. J. Kaiser, B. F. Koop, and L. Hood, *Science*, 1991, 254, 59.

A5. Large-Scale DNA Sequencing, T. Hunkapiller, R. J. Kaiser, B. F. Koop, and L. Hood, *Anal. Biotech.*, 1991, 2, 92–101.

A6. The Future of DNA Sequencing, L. M. Smith, *Science*, 1993, 262, 530–2.

A7. A system for rapid DNA sequencing with fluorescent chain-terminating dideoxynucleotides, J. M. Prober, G. L. Trainor, R. J. Dam, F. W. Hobbs, C. W. Robertson, R. J. Zagursky, A. J. Cocuzza, M. A. Jensen, and K. Baumeister, *Science*, 1987, 238, 336.

A8. Energy Transfer Primers: A New Fluorescence Labeling Paradigm for DNA Sequencing and Analysis, J. Ju, A. N. Glazer, and R. A. Mathies, *Nature Med.*, 1996, 2, 246–9.

A9. Fluorescence energy transfer dye-labeled primers for DNA sequencing and analysis, J. Ju, C. Ruan, C. W. Fuller, A. N. Glazer, and R. A. Mathies, *Proc. Natl. Acad. Sci. USA*, 1995, 92, 4347–51.

A10. Ultra-High-Speed DNA Sequencing Using Capillary Electrophoresis Chips, A. T. Woolley, and R. A. Mathies, *Anal. Chem.*, 1995, 67, 3676–80.

A11. Rapid Sizing of Short Tandem Repeat Alleles Using Capillary Array Electrophoresis and Energy-Transfer Fluorescent Primers, Y. Wang, J. Ju, B. A. Carpenter, J. M. Atherton, G. F. Sensabaugh, and R. A. Mathies, *Anal. Chem.*, 1995, 67, 1197–203.

A12. Design and Synthesis of Fluorescence Energy Transfer Dye-Labeled Primers and Their Application for DNA Sequencing and Analysis, J. Ju, I. Kheterpal, J. R. Scherer, C. Ruan, C. W. Fuller, A. N. Glazer, and R. A. Mathies, *Analytical Biochem.*, 1995, 231, 131–40.

A13. Energy Transfer Primers with 5- or 6-Carboxyrhodamine-6G as Acceptor Chromophores, S.-C. Hung, J. Ju, R. A. Mathies, and A. N. Glazer, *Analytical Biochem.*, 1996, 238, 165–70.

A14. Continuous, On-line DNA Sequencing Using Oligodeoxynucleotide Primers With Multiple Fluorophores, J. A. Brumbaugh, L. R. Middendorf, D. L. Grone, and J. L. Ruth, *Proc. Natl. Acad. Sci.*, 1988, 85, 5610–4.

A15. A Single Residue in DNA Polymerases of the *Escherichia coli* DNA Polymerase I Family is Critical for Distinguishing between Deoxy- and Dideoxyribonuleotides, S. Tabor, and C. C. Richardson, *Proc. Natl. Acad. Sci. USA*, 1995, 92, 6339–6343.

A16. Cassette Labeling for Facile Construction of Energy Transfer Fluorescent Primers, J. Ju, A. N. Glazer, and R. A. Mathies, *Nucleic Acids Res.*, 1996, 24, 1144–8.

A17. Electrophoretically Uniform Fluorescent Dyes for Automated DNA Sequencing, M. L. Metzker, J. Lu, and R. A. Gibbs, *Science*, 1996, 271, 1420–2.

A18. Comparison of Fluorescence Energy Transfer primers with Different Donor-Acceptor Dye Combinations, S. Hung, R. A. Mathies, and A. N. Glazer, *Analytical Biochemistry*, 1998, 255, 32–8.

A19. A Convenient Synthesis of Acetylenes: Catalytic Substitutions of Acetylenic Hydrogen with Bromoalkenes, Iodoarenes, and Bromopyridines, K. Sonogashira, Y. Tohda, and N. Hagihara, *Tetrahedron Lett.*, 1975, 4467–70.

A20. Stepwise Synthesis of Substituted Oligo (phenylenevinylene) via an Orthogonal Approach, T. Maddux, W. Li, and L. Yu, *J. Am. Chem. Soc.*, 1997, 119, 844–5.

A21. Synthesis of Sequence Specific Phenylacetylene Oligomers on an Insoluble Solid Support, J. K. Young, J. C. Nelson, and J. S. Moore, *J. Am. Chem. Soc.*, 1994, 116, 10841–2.

A22. Iterative Divergent/Convergent Approach to Linear Conjugated Oligomers by Successive Doubling of the Molecular Length: A Rapid Route to a 128 Å-Long Potential Molecular Wire, J. S. Schumm, D. L. Pearson, and J. M. Tour, *Angew. Chem., Int. Ed. Engl.*, 1994, 33, 1360–3.

A23. Soluble poly(1,4-phenyleneethynylene)s, R. Giesa, and R. C. Schulz, *Makromol Chem.*, 1990, 191, 857–67.

A24. Luminescent Alkoxy-Functionalized Polyphenylenes, J. L. Reddinger, and J. R. Reynolds, *Abstr. Papers Am Chem. Soc.*, 1996, 211, 530–1.

A25. Fluorescence Studies of Poly(p-phenyleneethynylene)s: The Effect of Andiracene Substitution, T. M. Swager, C. J. Gil, and M. S. Wrighton, *J. Phys. Chem.*, 1995, 99, 4886–93.

A26. Efficient Solid-State Photoluminescence in New Poly (2,5-dialkoxy-p-phenyleneethynylene)s, C. Weder, and M. S. Wrighton, *Macromolecules*, 1996, 29, 5157–65.

A27. Energy Transfer in Dendritic Macromolecules: Molecular Size Effects and the Role of an Energy Gradient, C. Devadoss, P. Bharathi, and J. S. Moore, *J. Am. Chem. Soc.*, 1996, 118, 9635–44.

A28. Phenylacetylene Dendrimers by the Divergent Convergent, and Double-Stage Convergent Methods, Z. Xu, M. Kahr, K. L. Walker, C. L. Wilkins, and J. S. Moore, *J. Am. Chem. Soc.*, 1994, 116, 4537–50.

A29. Conjugated Macromolecules of Precise Length and Constitution. Organic Synthesis for the Construction of Nanoarchitectures, J. M. Tour, *Chem. Rev.*, 1996, 96, 537–53.

A30. A Molecular Photonic Wire, R. W. Wagner, and J. S. Lindsey, *J. Am. Chem Soc.*, 1994, 116, 9759–60.

A31. Boron-dipyrromethene Dyes for Incorporation in Synthetic Multi-pigment Light-harvesting Arrays, R. W. Wagner, and J. S. Lindsey, *Pure & Appl. Chem.*, 1996, 68, 1373–80.

B1. S. C. Benson, P. Singh, A. N. Glazer, *Nucleic Acids Res.* 1993, 2I, 5727–35.

B2. J. Ju, A. N. Glazer, R. A. Mathies, *Nature Med.* 1996, 271, 246–9.

B3. M. L. Metzker, J. Lu, R. A. Gibbs, *Science* 1996, 271, 1420–2.

B4. L. G. Lee, S. L. Spurgeon, C. R. Heiner, S. C. Benson, B. B. Rosenblum, S. L. Menchen, R. J. Graham, A. Constantinescu, K. G. Upadhya, J. M. Cassel, *Nucleic Acids Research* 1997, 25, 2816–22.

B5. R. W. Wagner, J. S. Lindsey, *J. Am. Chem. Soc.* 1994, 116, 9759–60.

B6. T. M. Swager, C. J. Gil, M. S. Wrighton, *J. Phys. Chem.* 1995, 99, 4886–93.

B7. J. S. Schumm, D. L. Pearson, J. M. Tour, *Agnew. Chem., Int. Ed. Engl.* 1994, 33, 1360–3.

B8. J. M. Tour, *Chem. Rev.* 1996, 96, 537–53.

B9. C. Weder, M. S. Wrighton, *Macromolecules* 1996, 29, 5157–65.

B10. A. Treibs, F. H. Kreuzer, *Liebigs Ann. Chem.* 1968, 718, 208–23. BODIPY=4,4-difluoro-4-bora-3a,4a-diaza-s-indacene.

B11. T. Chen, J. H. Boyer, M. L. Trudell, *Heteroatom Chem.* 1997, 8, 51–4.

B12. K. Sonogashira, Y. Tohda, N. Hagihara, *Tetrahedron Lett.* 1975, 4467–70.

B13. M. B. Goldfinger, K. B. Crawford, T. M. Swager, *J. Am. Chem. Soc.* 1997, 119, 4578–4593.

B14. I. B. Campbell, *Organocopper Reagents: a Practical Approach* 1994, 217–35.

B15. M. S. Vollmer, F. Wurthuer, F. Effenberger, P. Emele, D. U. Meyer, e. al, *Chem. Eur. J.* 1998, 4, 260–9.

B16. M. S. Vollmer, F. Effenberger, T. Stumpfig, A. Hartschuh, H. Port, H. C. Wolf, *J. Org. Chem.* 1998, 63, 5080–7.

Appendix A

Through-bond Energy Transfer Dyes For Biotechnological Applications**

[**] A patent application entitled, "Through Bond Energy Transfer in Fluorescent Dyes for Labeling Biological Molecules" has been filed. We thank Dr C. I. Martinez (Baylor College of Medicine) for valuable discussions. Financial support for this work was provided by the NIH (HG0 1745) and The Robert A. Welch Foundation. A. B. thanks the Deutsche Forschungsgemeinschaft for a fellowship.

Figure 7A:
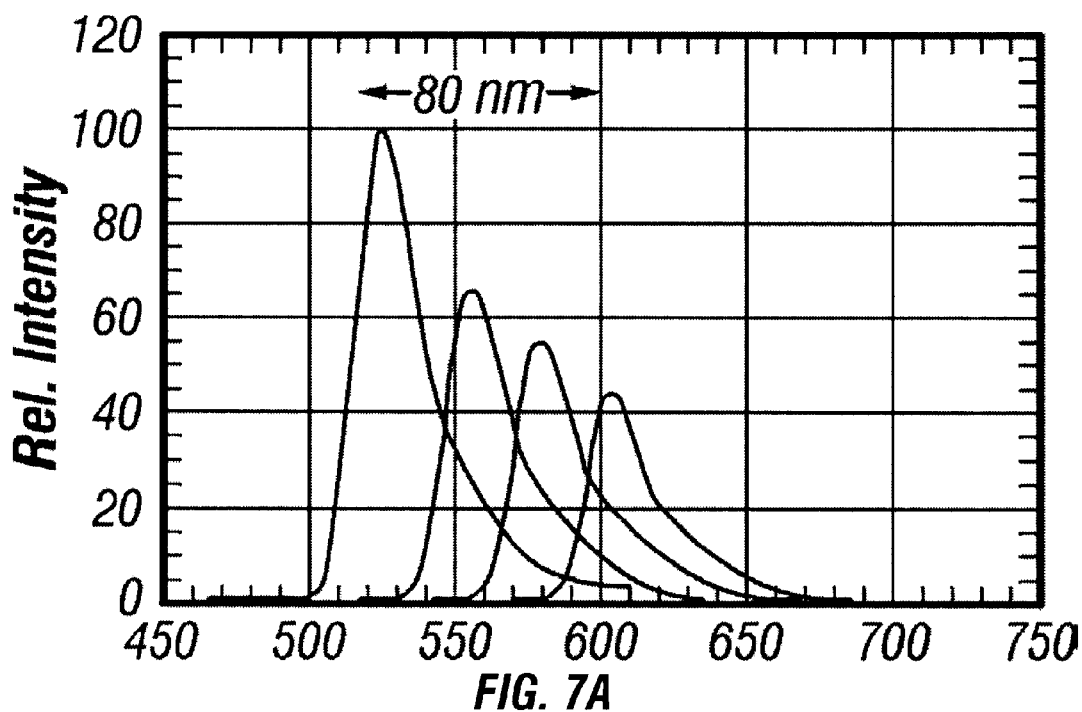
FIG. 7A shows that current dyes for DNA sequencing have overlapping fluorescence emissions spanning approximately 80 nm and decreasing intensities at longer wavelengths.
Figure 7B:
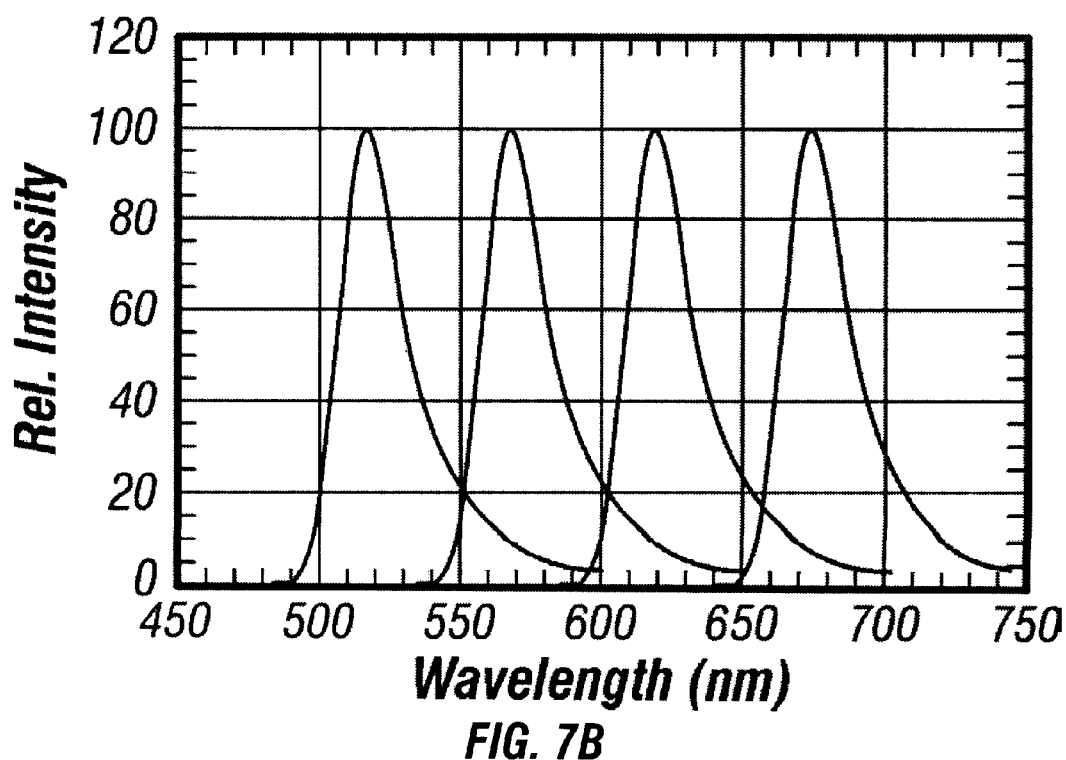
FIG. 7B shows that ideal dyes would be better resolved and fluoresce strongly with equal intensities.
Figure 8A:
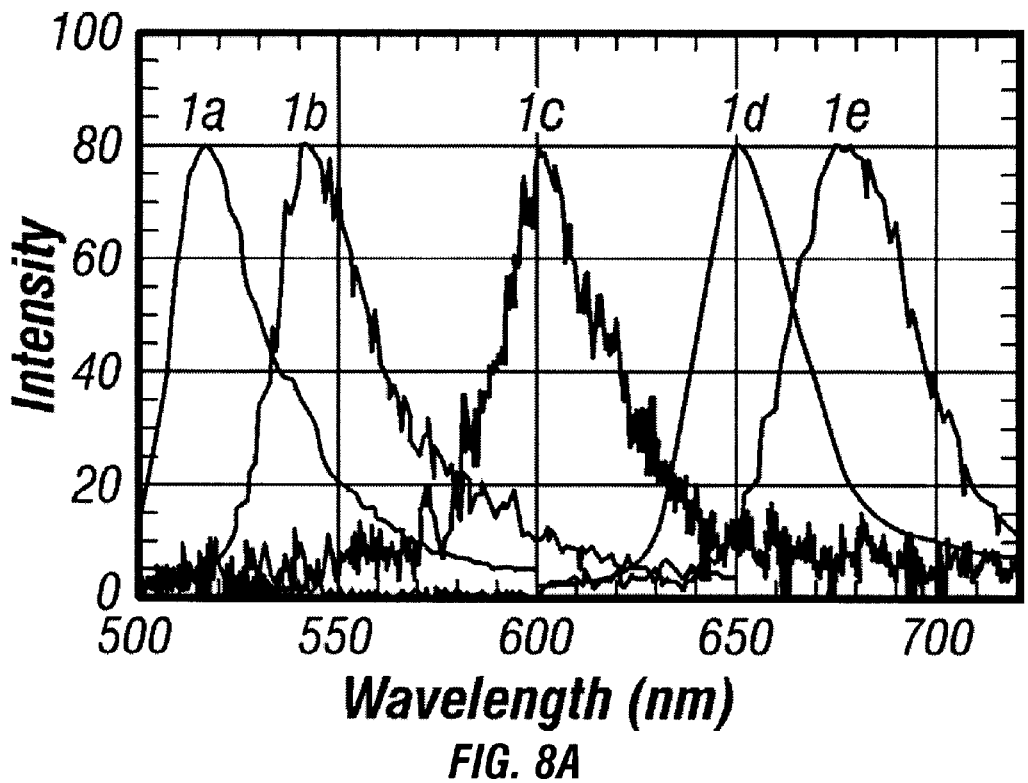
FIG. 8A shows the normalized fluorescence emission spectra (270 nm excitation) of 1 $\mu$M chloroform solutions of dyes 1a–e.
Figure 8B:
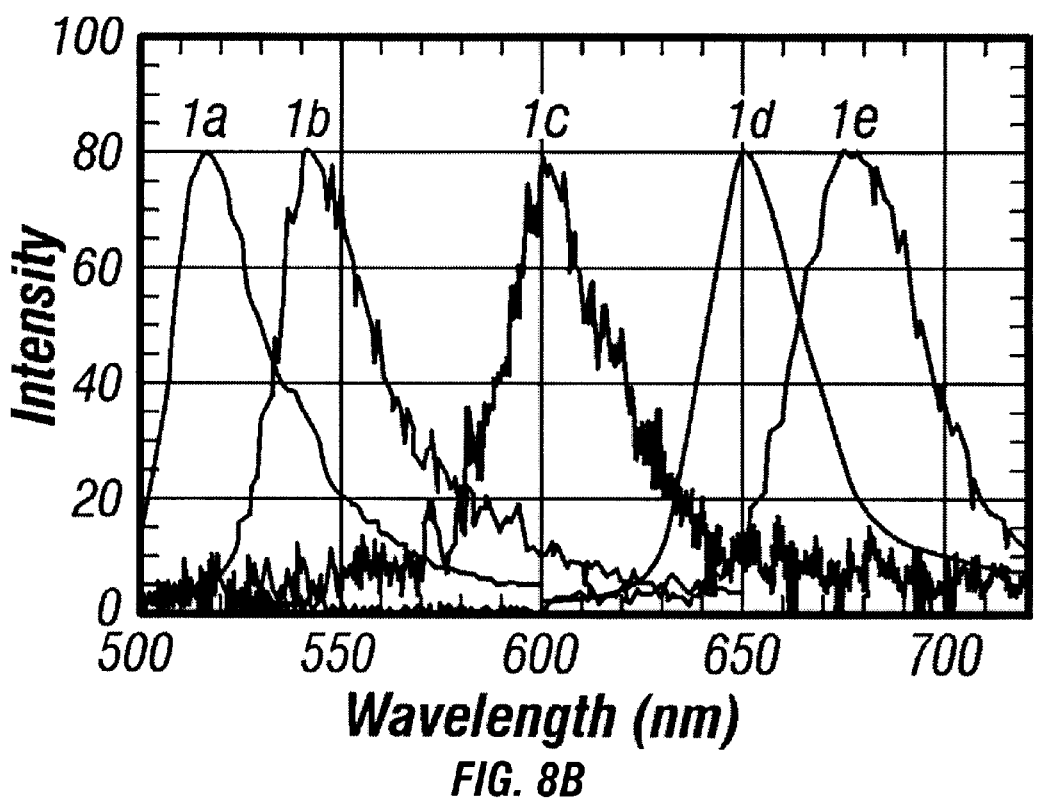
FIG. 8B shows the normalized fluorescence emission spectra (270 nm excitation) of 1 $\mu$M chloroform solutions of dyes 1a and 1e.
Figure 8C:
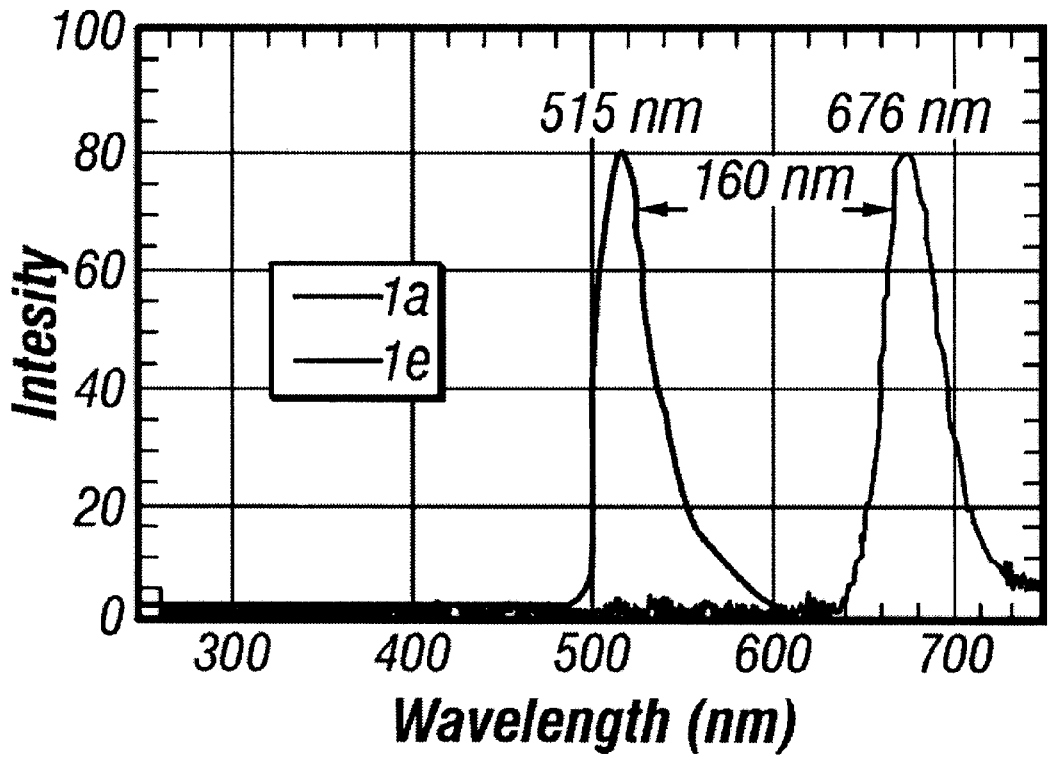
Figure 8D:
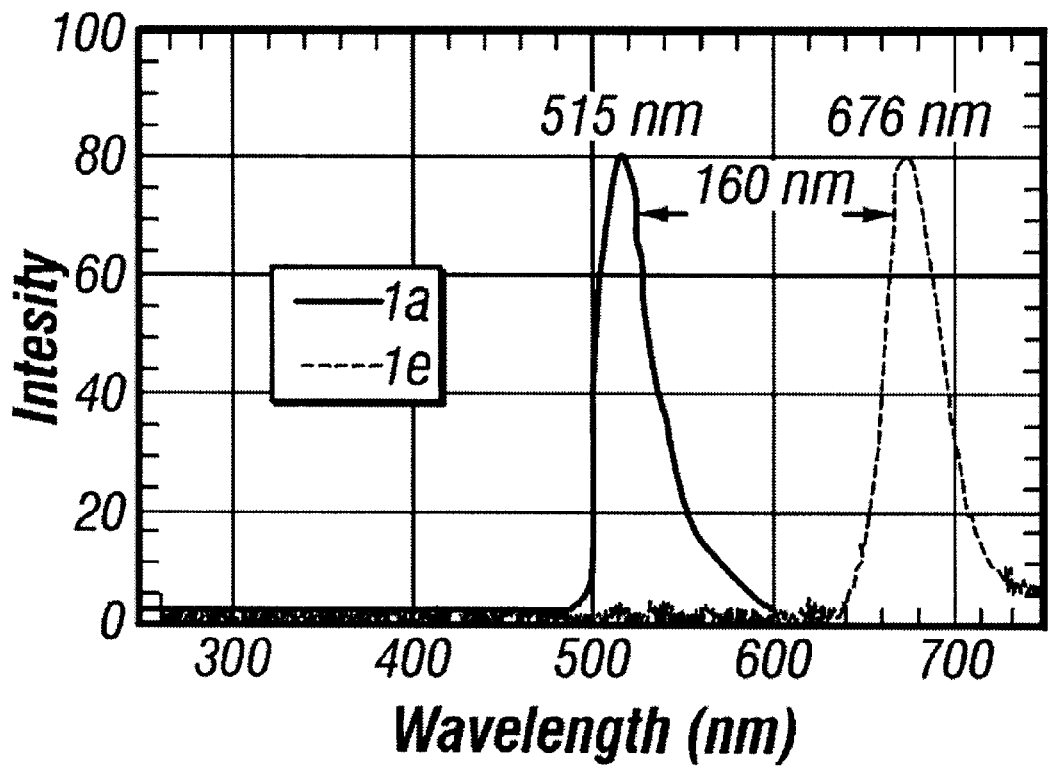
Figure 9A:
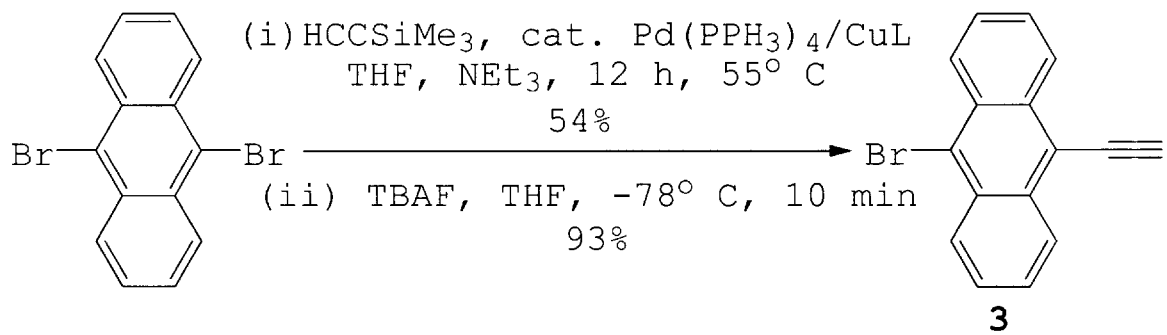
FIGS. 9A–D depicts the synthesis of dyes 1a–e.
Figure 9B:
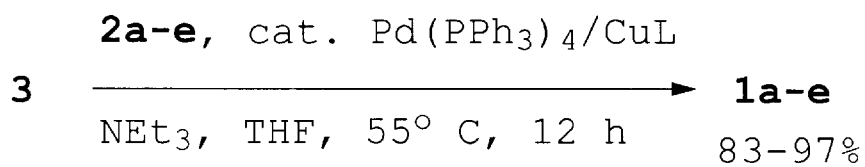
Figure 9C:
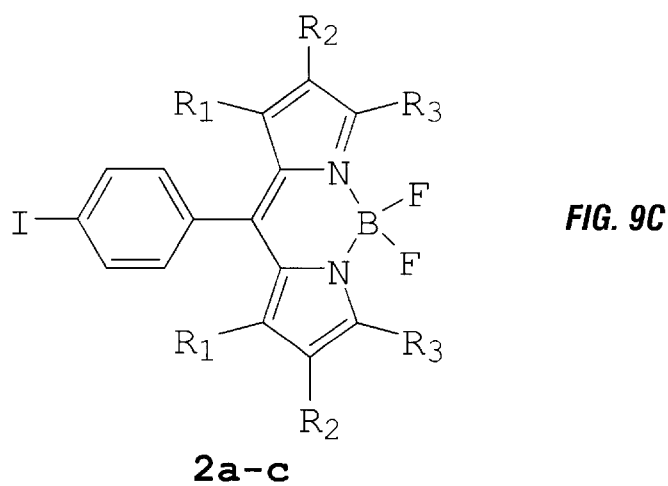
Figure 9D:
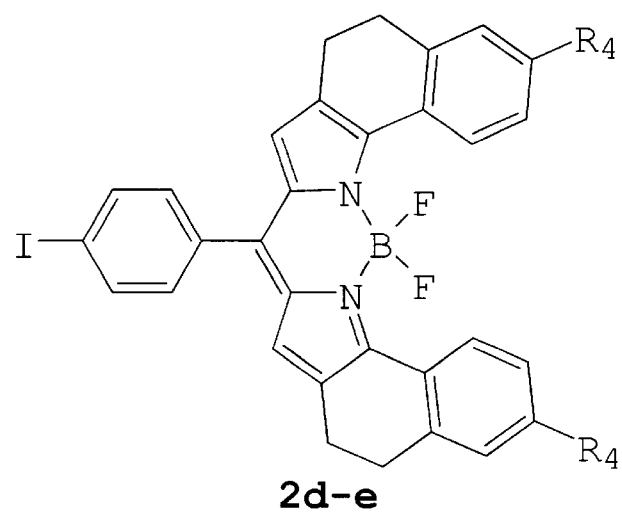
Figure 10:
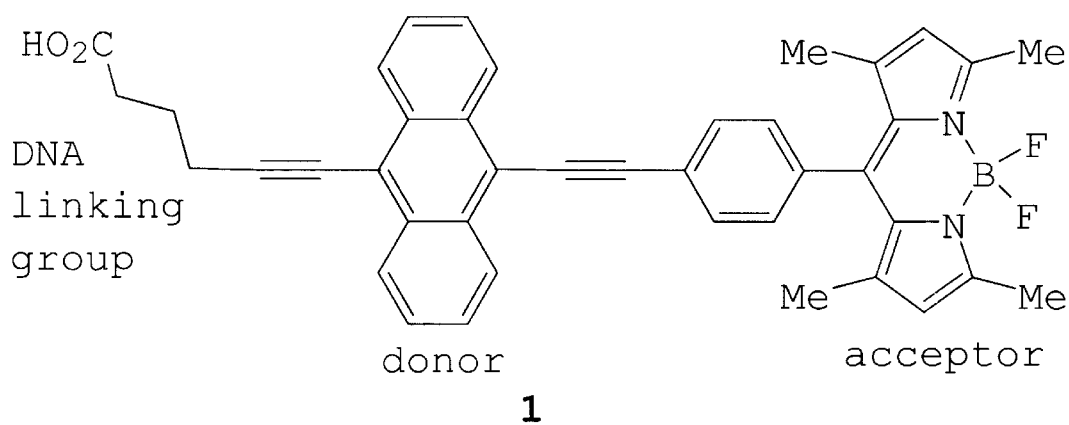
FIG. 10 shows a dye molecule containing a DNA linking group. The dye can capture light from a blue laser and emit at much longer wavelengths.

Fluorescent dyes are central to many applications in biotechnology. For instance, all of the methods being used for sequencing the human genome involve fluorescence detection,[1] as do the current technologies for visualizing DNA arrays for genomics. [2] However, the dyes that are currently available are far from perfect. The important case of automated DNA sequencing illustrates the type of limitation that is encountered. As DNA fragments emerge from chromatographic separation they are irradiated by a single laser source and the fluorescence of the dye-label is monitored. Two characteristics of the fluorescence emission properties are critical for such four-color sequencing schemes: resolution of $\lambda_{max\ emis}$ values for the dyes, and their fluorescence intensities. These two requirements place opposing constraints on the system. Resolution requires emissions at wavelengths that are distinct from each other and from that of the excitation source. For single dye systems, fluorescence intensities are inversely related to their $\lambda_{max\ emis}$ values. This is because longer wavelength fluorescence emissions correlate with longer wavelength absorption maxima that overlap less with the laser source. Through-space energy transfer dyes were developed to alleviate this problem, but still they require overlap of the donor emission with the acceptor absorption and this places constraints on the system. Consequently, the dye sets currently used in DNA sequencing, including the state-of-the-art through-space energy transfer systems [3] introduced in the last five years, [4–10] represent a compromise between overall resolution and intensity of the labels emitting at the longer wavelengths, as illustrated in FIG. 7a. This contrasts sharply with FIG. 7b, a representation of the type of spectroscopic performance that is sought after in this field.

Data presented in this paper illustrate that resolution/sensitivity issues are much easier to reconcile in dyes that exploit through-bond (rather than through-space) energy transfer. Through-bond energy transfer has been widely investigated in the context of new materials [11] and models for photosynthesis, [12–16] but, to the best of our knowledge, this paper is the first to introduce the concept of using through-bond energy transfer to produce dyes for biotechnological applications.

Commercial dyes for DNA sequencing are designed to collect light from an argon laser emitting at 488 or 514 nm. Breaking with this paradigm, our dye set 1a–e incorporates a light-harvesting group that absorbs irradiation at 266 nm corresponding to lasers that operate on frequency doubling techniques. [17] Use of such a laser source that emits at a relatively short wavelength, increases the λ-range available for detecting well-resolved fluorescence emissions. Anthracene derivatives were chosen as the donor for the following reasons. Anthracene has a strong UV absorption maximum at 250 nm ($\epsilon$=80,000 $M^{-1}$ $cm^{-1}$, in hexane), [18] and substituted anthracenes tend to have slightly higher $\lambda_{max\ abs}$. values. Consequently, this simple aromatic system has good spectroscopic properties to capture light at 266 nm. Anthracene derivatives are also cheap, easy to modify, and stable.

4,4-Difluoro-4-bora-3a,4a-diaza-s-indacene (BODIPY®) units [19] were selected for the acceptor portion of dyes set 1. These heterocycles tend to have strong, sharp fluorescence emissions, and they are compatible with sequencing methodologies (aqueous environments, thermocycling etc). [8] Syntheses of the requisite aryl iodide units 2a–c were achieved via routine modifications of known procedures. [20] Preparations of the compounds 2d and 2e will be reported separately.

Couplings of the donor (anthracene-derivative) and acceptor (BODIPY) fragments were only notable insofar as the procedures used were easy to perform. They exploit the fact that aryl iodides are more reactive than aryl bromides in Sonogashira couplings, hence selective reactions are possible (FIGS. 9a–9d). [21]

Some spectroscopic properties of the dyes 1a–e are shown in Table 1. UV absorption spectra for these compounds represent an almost perfect superimposition of the donor and acceptor components. However, only the fluorescence emission peak of the acceptor BODIPY fragment was observed for each of the dyes when they were excited at 270 nm; quantitatively, the energy transfer efficiency for all these systems is over 95%. [22] The fluorescence emission spectrum of anthracene has no significant overlap with the absorption spectrum of any of the BODIPY acceptors, therefore this energy transfer must be predominantly via a through-bond mechanism. [23] Consequently, the apparent Stokes' shifts for the dyes are far greater than observed in any through-space energy transfer system. Finally, the relative quantum yields [23] of these systems were all very similar. The mechanism of energy transfer is therefore likely to be similar for all the dyes in this series.

Electrochemical data were also collected for compounds 1a–e. Briefly, two step reduction and oxidation processes were observed indicative of the anthracene and BODIPY fragments behaving as independent entities. For instance, all five dyes showed a partially reversible oxidation between 0.92 and 0.97 V (vs ferrocene in $CH_2Cl_2$) and the oxidation potential for 9-bromo-10-ethynylanthracene 3 under the same conditions was measured as 0.95 V.

Overall, these spectroscopic and electrochemical data indicate that the components of dyes 1a–e behave as two distinct conjugated systems. However, energy transfer between the donor and acceptor fragments occurs with minimal fluorescence leakage from the donor. The $\lambda_{max\ emis}$. values for these dyes span a 161 nm range; this is approximately twice the corresponding {80 nm} range observed for the classical dyes used for DNA sequencing (FAM, JOE, TAMRA, ROX). [4] FIGS. 8a–d shows superimposed fluorescence spectra to illustrate the resolution involved. The relative intensities of dyes 1a–e (0.81:1.00:0.05:0.23:0.20) correspond to the relative intensities of the acceptor fragments. Apparently, unlike through-space energy transfer dyes, their intensities do not diminish with their apparent Stokes' shifts.

The dyes described here are prototypes for labels that could be used in automated DNA sequencing, but several obvious modifications need to be made to produce viable systems. In absolute terms, the intensities of these dyes are less than desired. Further experimentation is in progress to identify through-bond energy transfer dyes composed of other donor/acceptor combinations to give improved resolution and fluorescence intensities. Other desirable changes include ones to increase the water solubilities of these systems, and to standardize their gel mobilities for accurate base-calling. Moreover, a facile method for attachment of the dyes to DNA must be developed. In systems 1 the bromine functionality on the anthracene units is present to allow attachment of the dyes to DNA; thus, compound 1a has been transformed into the acid 4, and coupling of this to DNA is being investigated. These issues are, however, peripheral to the fundamental conclusion of this paper: through-bond energy transfer dyes have the potential to overcome problems that cannot be adequately addressed using single dye systems or through-space energy transfer cassettes.

Keywords: fluorescence•dyes•DNA sequencing•fluorescence energy transfer

TABLE 1

Salient Spectral Data for Compounds 1[a].

| compound | $\lambda_{max\ abs.}$ (nm) | $\epsilon$ ($M^{-1}$ $cm^{-1}$) | $\lambda_{max\ emis.}$ (nm) | apparent Stokes shift[b] (nm) | energy transfer efficieny[c] | relative quantum yield[d] |
|---|---|---|---|---|---|---|
| 1a | 270 | 73000 | 515 | 245 | >95 | 0.09 |
|  | 504 | 60000 |  |  |  |  |
| 1b | 270 | 88500 | 544 | 274 | >95 | 0.09 |
|  | 528 | 65000 |  |  |  |  |
| 1c | 267 | 89000 | 600 | 333 | >95 | 0.10 |
|  | 552 | 43000 |  |  |  |  |

TABLE 1-continued

Salient Spectral Data for Compounds 1[a].

| com-<br>pound | $\lambda_{max\ abs.}$<br>(nm) | $\epsilon$<br>($M^{-1}$<br>$cm^{-1}$) | $\lambda_{max\ emis.}$<br>(nm) | apparent<br>Stokes<br>shift[b]<br>(nm) | energy<br>transfer<br>efficieny[c] | relative<br>quan-<br>tum<br>yield[d] |
|---|---|---|---|---|---|---|
| 1d | 268 | 67000 | 650 | 382 | >95 | 0.11 |
|  | 636 | 70000 |  |  |  |  |
| 1e | 268 | 57000 | 676 | 408 | >95 | 0.11 |
|  | 660 | 72000 |  |  |  |  |

[a]All data measured in chloroform.
[b]From the absorption maxima in the 267–270 nm region.
[c]Percentage energy transfer efficiency = {1 − (fluorescence intensity of donor in cassette/fluorescence intensity of equimolar donor irradiated under same conditions) × 100.[22]
[d]Relative quantum yield = (observed fluorescence intensity of 1 when irradiated at 270 nm/observed fluorescence intensity of 1 when irradiated at absorption maxima of the acceptor) × (extinction coefficient of 1 at $\lambda_{max}$ abs. of acceptor/extinction coefficient of 1 of the donor at 270 nm).[23]

diagram 1

1a–e

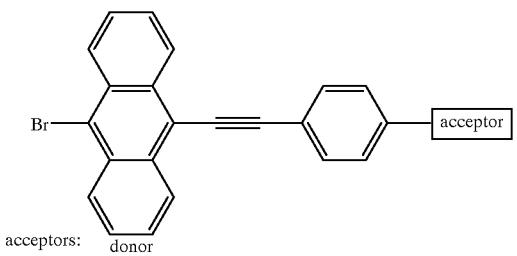

acceptors: donor

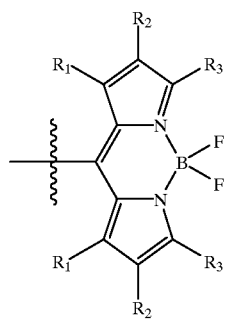

| | R[1] | R[2] | R[3] |
|---|---|---|---|
| a | Me | H | Me |
| b | Me | Et | Me |
| c | H | H | 2-MeOC$_6$H$_4$ |

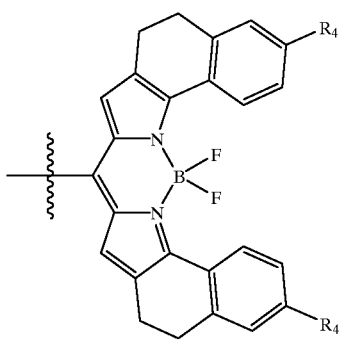

| | R[4] |
|---|---|
| d | H |
| e | OMe | diagram 2

4a

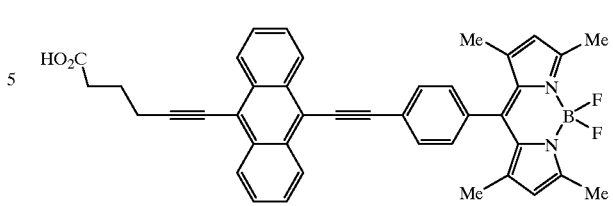

diagram for abstract

1

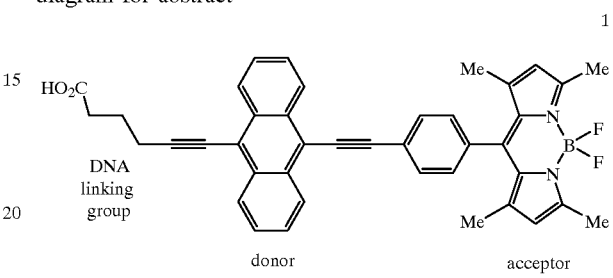

donor        acceptor

Donor-acceptor fluorescent dye systems like 1 capture light from a blue laser and emit at much longer wavelengths. Huge apparent Stokes' shifts are observed and the dispersion of fluorescence emission maxima that can be observed for a single laser source is correspondingly large. Through-bond energy transfer dyes such as this can give well-resolved and intensely fluorescent labels for DNA sequencing and other applications.

[1] L. M. Smith, J. Z. Sanders, R. J. Kaiser, P. Hughes, C. Dodd, C. R. Connell, C. Heiner, S. B. Kent, L. E. Hood, *Nature* 1986, 321, 674–9.
[2] R. Drmanac, I. Labat, I. Brukner, R. Crkvenjakov, *Genomics* 1989, 4, 114–28.
[3] Throughout "donor groups" are those which collect the irradiation, and "acceptor groups" are those which harvest it from the donor and emit. The terms "through-space" and "through-bond" refer to the mechanisms by which energy is transferred from the donor to the acceptor.
[4] J. Ju, C. Ruan, C. W. Fuller, A. N. Glazer, R. A. Mathies, *Proc. Natl. Acad. Sci. USA* 1995, 92, 4347–51.
[5] S. Menchen, L. Lee, P. Thelsen, S. Benson, K. Upadhya, T. Constantinescu, R. Graham, S. Spurgeon, B. Rosenblum, S. Koepf, R. O'Neill, *PE Applied Biosystems, technical report* 1996, 1–4.
[6] J. Ju, A. N. Glazer, R. A. Mathies, *Nature Med.* 1996, 2, 246–9.
[7] J. Ju, I. Kheterpal, J. R. Scherer, C. Ruan, C. W. Fuller, A. N. Glazer, R. A. Mathies, *Analytical Biochem.* 1995, 231, 131–40.
[8] M. L. Metzker, J. Lu, R. A. Gibbs, *Science* 1996, 271, 1420–2.
[9] L. G. Lee, S. L. Spurgeon, C. R. Heiner, S. C. Benson, B. B. Rosenblum, S. M. Menchen, R. J. Graham, A. Constantinescu, K. G. Upadhya, J. M. Cassel, *Nucleic Acids Research* 1997, 25, 2816–22.
[10] B. B. Rosenblum, L. G. Lee, S. L. Spurgeon, S. H. Khan, S. M. Menchen, C. R. Heiner, S. M. Chen, *Nucleic Acids Research* 1997, 25, 4500–4.
[11] J. M. Tour, *Chem. Rev.* 1996, 96, 537–53.
[12] R. W. Wagner, J. S. Lindsey, *Pure & Appl. Chem.* 1996, 68, 1373–80.
[13] M. S. Vollmer, F. Würthner, F. Effenberger, P. Emele, D. U. Meyer, T. Stümpfig, H. Port, H. C. Wolf, *Chem. Eur. J.* 1998, 4, 260–9.

[14] M. S. Vollmer, F. Effenberger, T. Stümpfig, A. Hartschuh, H. Port, H. C. Wolf, *J. Org. Chem.* 1998, 63, 5080–7.
[15] F. Li, S. I. Yang, Y. Ciringh, J. Seth, C. H. Martin, D. L. Singh, D. Kim, R. R. Birge, D. F. Bocian, D. Holten, J. S. Lindsey, *J. Am. Chem. Soc.* 1998, 120, 10001–17.
[16] R. W. Wagner, J. Seth, S. I. Yang, D. Kim, D. F. Bocian, D. Holten, J. S. Lindsey, *J. Org. Chem.* 1998, 63, 5042–9.
[17] B. D. Sinclair, *Optical Materials* 1999, 11, 217–33.
[18] K. Lauer, M. Horio, *Ber. Dtsch. Chem. Ges.* 1936, 69, 130–137.
[19] A. Treibs, F.-H. Kreuzer, *Liebigs Ann. Chem.* 1968, 718, 208–23.
[20] L. H. Thoresen, H. Kim, M. B. Welch, A. Burghart, K. Burgess, *Synlett* 1998, 1276–8.
[21] M. B. Goldfinger, K. B. Crawford, T. M. Swager, *J. Am. Chem. Soc.* 1997, 119, 4578–4593.
[22] J.-L. Mergny, T. Garestier, M. Rougée, A. V. Lebedev, A. V. Chassignol, N. T. Thuong, C. Héléne, *Biochemistry* 1994, 33, 15321–8.
[23] S.-i. Kawahara, T. Uchimaru, S. Murata, *Chem. Commun.* 1999, 8, 563–4.

Throughout "donor groups" are those which collect the irradiation, and "acceptor groups" are those which harvest it from the donor and emit. The terms "through-space" and "through-bond" refer to the mechanisms by which energy is transferred from the donor to the acceptor.

We claim:

1. A fluorescent dye comprising:

an anthracene derivative; and
   a BODIPY fragment; wherein:
      the anthracene derivative and the BODIPY fragment are conjugated to each other;
      the BODIPY fragment is

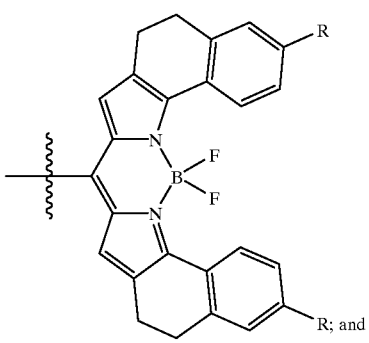

R is hydrogen or methoxy.

2. A fluorescent dye consisting of the formula:

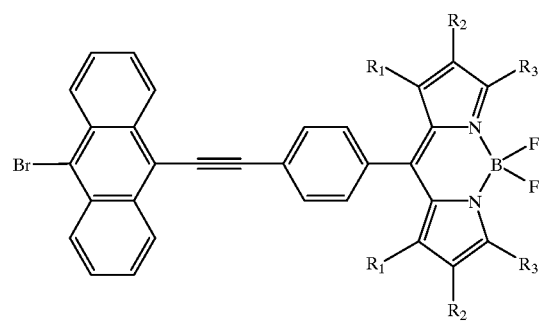

wherein:
   $R^1$ is methyl or hydrogen;
   $R_2$ is hydrogen or ethyl; and
   $R_3$ is methyl or 2-methoxyphenyl.

3. The dye of claim 1, wherein the dye is:

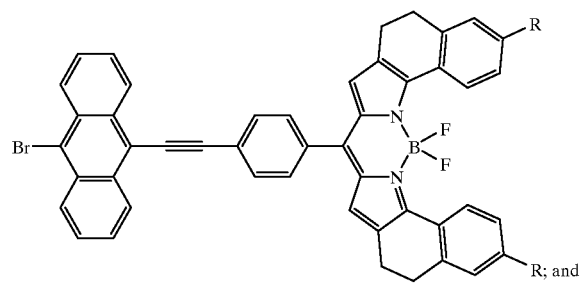

R is hydrogen or methoxy.

4. A fluorescent dye comprising an anthracene derivative, a BODIPY fragment, and a functional group for covalently bonding the dye to a molecule; wherein the functional group is a bromine group, a succinimidyl ester group, or a carboxylic acid group.

5. The dye of claim 4, wherein the functional group is a succinimidyl ester group.

6. The dye of claim 4, wherein the functional group is a carboxylic acid group.

7. The dye of claim 6, wherein the dye is

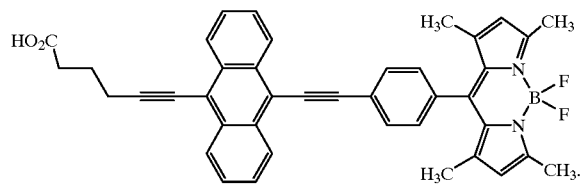

8. The dye of claim 4, wherein the functional group is a bromine group.

* * * * *

UNITED STATES PATENT AND TRADEMARK OFFICE
CERTIFICATE OF CORRECTION

PATENT NO. : 6,340,750 B1
DATED : January 22, 2002
INVENTOR(S) : Kevin Burgess et al.

It is certified that error appears in the above-identified patent and that said Letters Patent is hereby corrected as shown below:

Title page,
Item [56], References Cited, OTHER PUBLICATIONS, after "*Chem*", insert -- . --; and after "Meyer", delete "e. al," and insert -- et al., --; and after "*Eur.*", delete ".".

Column 4,
Line 2, after "$BF_3$", delete ".", and insert -- • --.
Line 6, after "cat", insert -- . --.

Column 5,
Line 26, the portion of the sentence reading "these primers require seven more coupling steps than are required to generate the primer sequence" should be italicized.
Line 39, before "An", delete ".", and after "wavelength)" insert -- . -- and insert a space.

Column 7,
Line 17, after "ohgomeric", insert -- , --.
Line 36, after "emission", delete "max", and insert -- $_{max}$ --.
Line 63, after "2ab.", delete "the", and insert -- The --.

Column 8,
Line 11, after "$BF_3$", delete ".", and insert -- • --.
Line 18, after "reactions", delete "indicted" and insert -- indicated --.
Line 35, the portion of the word "meta" in the word "meta-substituted" should be italicized.
Line 37, the portion of the word "para" in the word "para-orientation" should be italicized.

Column 10,
Line 25, after "M+", insert a space before "611".
Line 26, after "216° C", delete ".".
Line 36, after "967", delete "," and insert -- . --.

Column 11,
Line 61, after "Poly(" the "p" in the word "p-phenyleneethynylene" should be italicized.
Line 66, the letter "p" between "s-dialkoxy-" and "-phenyleneethynylene" should be italicized.

UNITED STATES PATENT AND TRADEMARK OFFICE
CERTIFICATE OF CORRECTION

PATENT NO. : 6,340,750 B1
DATED : January 22, 2002
INVENTOR(S) : Kevin Burgess et al.

It is certified that error appears in the above-identified patent and that said Letters Patent is hereby corrected as shown below:

Column 12,
Line 13, after "*Chem*", insert -- . --.
Line 47, after "Meyer", delete "e. al," and insert -- et al., --.

Column 13,
Line 4, the word "resolution" should be italicized.
Line 5, the word "intensifies" should be italicized.

Signed and Sealed this

Twenty-fifth Day of March, 2003

JAMES E. ROGAN
*Director of the United States Patent and Trademark Office*